(12) United States Patent  (10) Patent No.: US 8,444,879 B2
Ehlis et al.  (45) Date of Patent: May 21, 2013

(54) TRIAZINE DERIVATIVES

(75) Inventors: Thomas Ehlis, Freiburg (DE); Elek Borsos, Birsfelden (CH)

(73) Assignee: BASF SE, Ludwigshafen (DE)

( * ) Notice: Subject to any disclaimer, the term of this patent is extended or adjusted under 35 U.S.C. 154(b) by 1077 days.

(21) Appl. No.: 12/227,042

(22) PCT Filed: May 2, 2007

(86) PCT No.: PCT/EP2007/054239
§ 371 (c)(1),
(2), (4) Date: Nov. 5, 2008

(87) PCT Pub. No.: WO2007/128744
PCT Pub. Date: Nov. 15, 2007

(65) Prior Publication Data
US 2009/0124576 A1  May 14, 2009

(30) Foreign Application Priority Data
May 8, 2006 (EP) .................................. 06113634

(51) Int. Cl.
C07D 251/52 (2006.01)
C07D 251/70 (2006.01)
C07D 403/12 (2006.01)
C07D 403/14 (2006.01)
A61Q 17/04 (2006.01)
A61K 8/49 (2006.01)

(52) U.S. Cl.
USPC ...... 252/301.23; 252/405; 524/100; 544/198; 544/209

(58) Field of Classification Search
USPC ........... 544/198, 209, 196; 514/245; 524/100; 252/301.23, 405
See application file for complete search history.

(56) References Cited

U.S. PATENT DOCUMENTS

| 4,843,150 A | 6/1989 | Hihara et al. | 534/634 |
| 4,963,659 A | 10/1990 | Tzikas | 534/618 |

(Continued)

FOREIGN PATENT DOCUMENTS

| EP | 0818450 | 1/1998 |
| GB | 1353051 | 5/1974 |

OTHER PUBLICATIONS

Derwent Abstract No. 2006-651098 [68] for JP 2006208887, Aug. 10, 2006.

(Continued)

*Primary Examiner* — Venkataraman Balasubramanian
(74) *Attorney, Agent, or Firm* — Shiela A. Loggins

(57) ABSTRACT

Disclosed are triazine derivatives of formula (1)

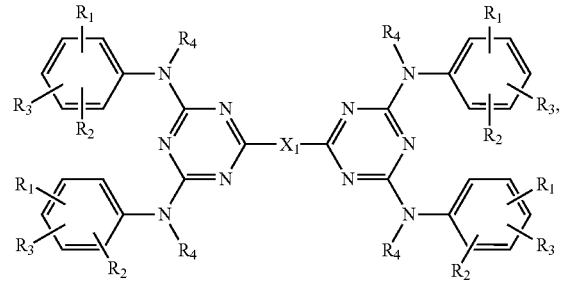

wherein
$X_1$ is a bivalent radical of formula

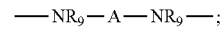 (1a)
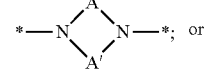 (1b)
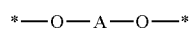 (1c)

A and A' independently from each other are unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene; or $C_5$-$C_{10}$arylene-($C_1$-$C_{12}$alkylene);
$R_1$ is a radical of formula (1d)

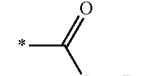

(1e)

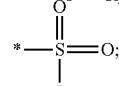

(1f)

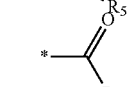

(1g)

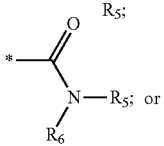

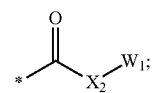

(1h)

$R_2$ and $R_3$ independently from each other are hydrogen; $C_1$-$C_{12}$alkyl; $OR_7$; $NR_7R_8$; $C_6$-$C_{10}$aryl;
$X_2$ is O, or NH;
$W_1$ is $C_1$-$C_{20}$alkyl; or a group Sp-Sil;
Sp is a straight-chain or branched saturated or single or multiple unsaturated $C_3$-$C_{12}$ hydrocarbon;
Sil is a silane; an oligosiloxane; or a polysiloxane moiety; and
$R_4$, $R_5$, $R_6$, $R_7$, $R_8$ and $R_9$ independently from each other are hydrogen; $C_1$-$C_{12}$alkyl; or $C_3$-$C_{12}$cycloalkyl.

14 Claims, No Drawings

U.S. PATENT DOCUMENTS

| | | | | |
|---|---|---|---|---|
| 6,153,364 | A | * | 11/2000 | Goswami et al. ............. 430/434 |
| 6,153,365 | A | * | 11/2000 | Goswami et al. ............. 430/455 |
| 6,232,052 | B1 | * | 5/2001 | Goswami et al. ............. 430/461 |
| 6,232,053 | B1 | * | 5/2001 | Goswami et al. ............. 430/486 |
| 6,395,461 | B1 | * | 5/2002 | Goswami et al. ............. 430/460 |
| 6,395,462 | B2 | * | 5/2002 | Goswami et al. ............. 430/463 |
| 2002/0055071 | A1 | * | 5/2002 | Nakai et al. ................... 430/429 |
| 2004/0110102 | A1 | * | 6/2004 | Okano et al. .................. 430/460 |
| 2007/0149528 | A1 | * | 6/2007 | Penney et al. ................. 514/241 |
| 2008/0145324 | A1 | * | 6/2008 | Richard et al. ................. 424/59 |

OTHER PUBLICATIONS

English language abstract of JP 2202966, Aug. 13, 1990.

English language abstract of EP 0818450, Jan. 14, 1998.

\* cited by examiner

TRIAZINE DERIVATIVES

The present invention relates to specific triazine derivatives, preparation of these compounds, the preparation of micronized particles of the new tirazine derivatives and cosmetic compositions comprising these triazine derivatives.

The triazine derivatives correspond to formula

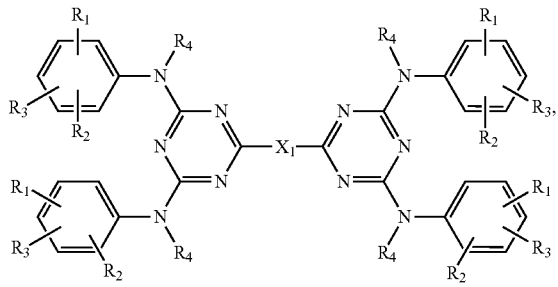
(1)

wherein
$X_1$ is a bivalent radical of formula

(1a)

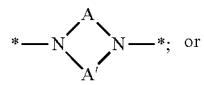
(1b)

or

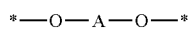
(1c)

A and A' independently from each other are unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene; or $C_5$-$C_{10}$arylene-($C_1$-$C_{12}$alkylene);

$R_1$ is a radical of formula

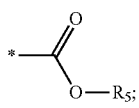
(1d)

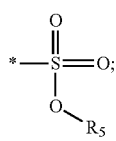
(1e)

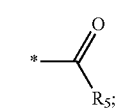
(1f)

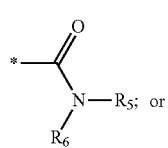
(1g)

or

(1h)

$R_2$ and $R_3$ independently from each other are hydrogen; $C_1$-$C_{12}$alkyl; $OR_7$; $NR_7R_8$; $C_6$-$C_{10}$aryl;

$X_2$ is O, or NH;

$W_1$ is $C_1$-$C_{20}$alkyl; or a group Sp-Sil;

Sp is a straight-chain or branched saturated or single or multiple unsaturated $C_3$-$C_{12}$ hydrocarbon;

Sil is a silane; an oligosiloxane; or a polysiloxanes moiety; and $R_4$, $R_5R_6$, $R_7$, $R_8$ and $R_9$ independently from each other are hydrogen; $C_1$-$C_{12}$alkyl; or $C_3$-$C_{12}$cycloalkyl.

$C_1$-$C_{12}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl or dodecyl.

$C_6$-$C_{10}$aryl is for example naphthyl or preferably phenyl.

$C_1$-$C_{12}$alkylene is for example methylene, ethylene, propylene, isopropylene, n-butylene, sec-butylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene, decylene or dodecylene.

Alkylene may be straight-chain, branched, or, from $C_5$alkyl upwards, monocyclic or polycyclic, and may be interrupted by hetero atoms, such as such as O, S, —CO—, N, NH, $NR_x$, —OCO—, —CO($OR_x$)—, —$CONR_x$—, —($R_x$) NC(O)—; for example $C_1$-$C_{10}$alkylene may be a bivalent radical such as: —$CH_2CH_2$—O—$CH_2CH_2$—O—$CH_2CH_2$—, —$CH_2CH_2$—O—$CH_2CH_2$—, —$CH_2CH_2$—O—$CH_2$—, —$CH_2$—O—$CH_2$—, —$CH_2CH_2$—$CH_2CH_2$—O—$CH_2$—$CH_2$—, —$CH_2CH_2$—CH($N(CH_3)_2$)—$CH_2$—$CH_2$—, $CH_2$—$NH_2$—$CH_2$—$CH_2$, —$CH_2CH_2$—NH—$CH_2CH_2$—, —$CH_2CH_2$—$NCH_3$—$CH_2CH_2$—, —CO—$CH_2$—, —$CH_2CO$—, —$CH_2CH_2$—NHCO—$CH_2CH_2$—, —$CH_2CH_2$—CONH—$CH_3$—$CH_2CH_2$—, —$CH_2CH_2$—$NCH_3CO$—$CH_2CH_2$—, —$CH_2CH_2$—$CONCH_3$—$CH_3$—$CH_2CH_2$—, —$CH_2$—NHCO—$CH_2CH_2$—, —$CH_2CH_2$—NHCO—$CH_2$—, —$CH_2CH_2$—CONH—$CH_2$— or —$CH_2$—CONH—$CH_2CH_2$—. $R_x$ is hydrogen or $C_1$-$C_{12}$alkyl.

$C_5$-$C_{10}$cycloalkylene is for example cyclopentylene, cyclohexylene, cycloheptylene or cyclooctylene.

$C_6$-$C_{10}$arylene is for example naphthylene like

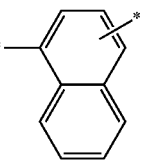 or 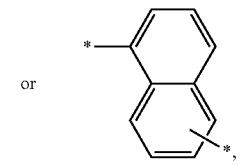

or preferably phenylene.

Preferred are compounds of formula (1) wherein
$R_1$ is a radical of formula

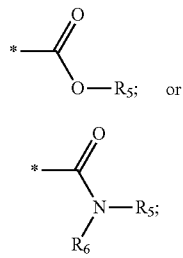

(1d)

(1g)

wherein
$R_5$ and $R_6$ independently from each other are hydrogen; or $C_1$-$C_5$alkyl; and more preferably, wherein
$R_5$ is $C_1$-$C_5$alkyl; or hydrogen; and
$R_6$ is hydrogen.

In formula (1)
$X_1$ is preferably a radical of formula (1b), wherein
A and A' are $C_1$-$C_4$alkylene; or wherein
$X_1$ is preferably a radical of formula (1a), wherein
A is $C_1$-$C_5$alkylene; or phenylene; and
$R_9$ is hydrogen.

Most preferably in formula (1)
$X_1$ is selected from

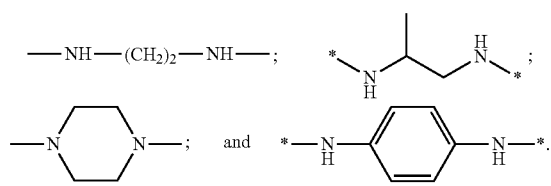

Most preferred are compounds of formula (1), wherein $R_2$, $R_3$ and $R_4$ are hydrogen.

Preferred are also compounds of formula (1), wherein
Sil is the group $SiR_{10}R_{11}R_{12}$, wherein
$R_{10}$, $R_{11}$ and $R_{12}$ each independently are $C_1$-$C_6$alkyl; $C_1$-$C_6$alkoxy; or phenyl; or an oligosiloxane of formula —$SiMe_m(OSiMe_3)_n$; or an oligosiloxane of the formulae

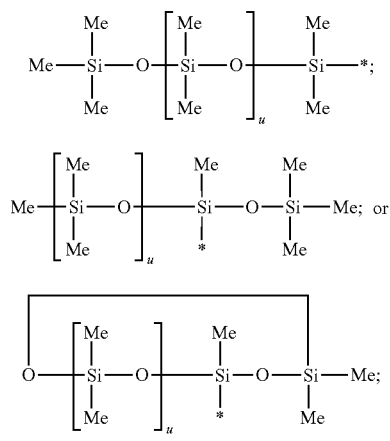

(1i)

(1k)

(1l)

wherein
Me is methyl;
m is 0; 1; or 2;
n is 1; 2; or 3;
m+n are 3; and
u is 0 to 6.

Very most preferred are compounds of formula

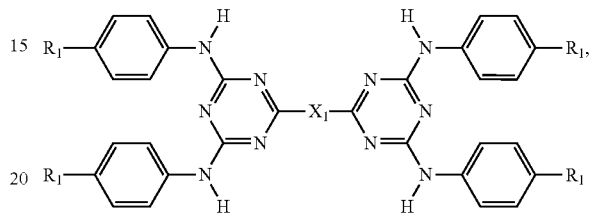

(2)

wherein
$R_1$ is a radical of formula

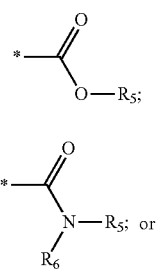

(1d)

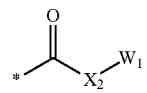

(1g)

(1h)

$X_1$ is radical of formula (1a) —$NR_9$-A-$NR_9$—; (1c)*-O-A-O-*; and

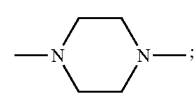

A, $W_1$, $X_2$ and $R_9$ are defined as in formula (1); and
$R_5$ and $R_6$ independently from each other are hydrogen; or $C_1$-$C_4$alkyl.

Preferred are compounds of formula (2), wherein
$R_1$ is a radical of formula

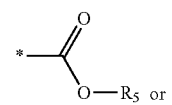

(1d)

-continued
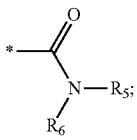
(1g)
$X_1$ is selected from
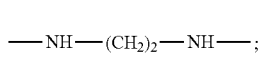; 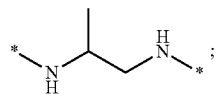
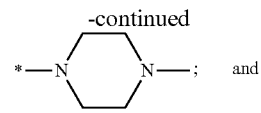; and
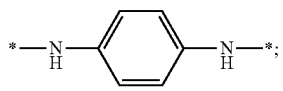
and
$R_5$ and $R_6$ independently from each other are hydrogen; or $C_1$-$C_4$alkyl.
Examples of compounds of formula (1) are listed in the Table below:
TABLE 1
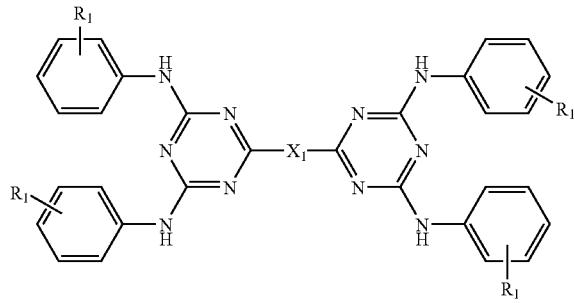
| Compound of formula | $R_1$ | $X_1$ |
|---|---|---|
| (3) | —CO(O)—$C_2H_5$ | 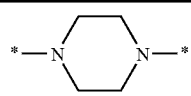 |
| (4) | —CO(O)—$C_2H_5$ | —NH—$(CH_2)_2$—NH— |
| (5) | —CO(O)—$C_2H_5$ | 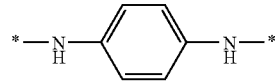 |
| (6) | —CO—$NH_2$ | 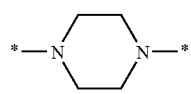 |
| (7) | —CO—$NH_2$ | —NH—$(CH_2)_2$—NH— |
| (8) | —CO(O)—$C_2H_5$ | 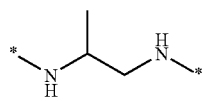 |
| (9) | 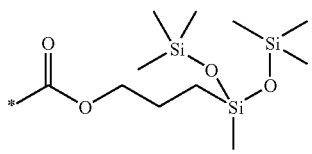 | 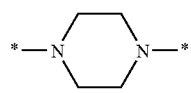 |
| (10) | 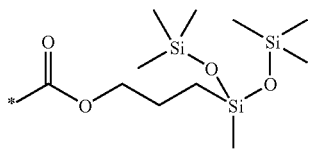 | 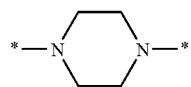 |

TABLE 1-continued
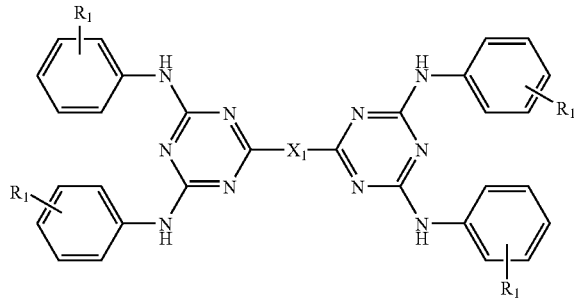
| Compound of formula | R₁ | X₁ |
|---|---|---|
| (11) | 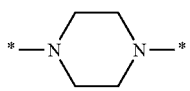 | 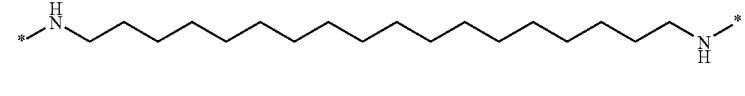 |
| (12) | 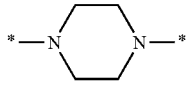 | 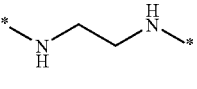 |
| (13) | —CO(O)—CH₃ | 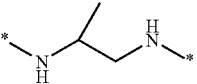 |
| (14) |  | 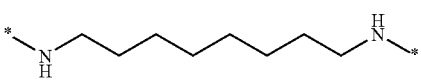 |
| (15) | 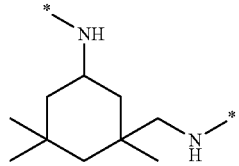 | |
| (16) | | |
| (17) | | |
| (18) | | |

TABLE 1-continued
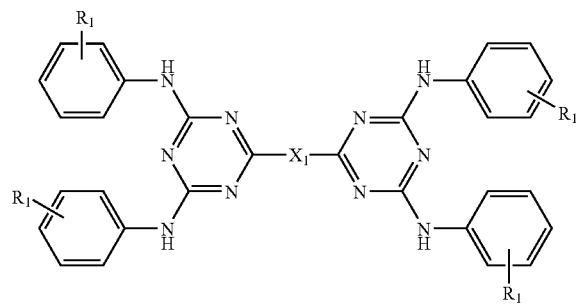
| Compound of formula | R₁ | X₁ |
|---|---|---|
| (19) | | |
| (20) | | |
| (21) | | |
| (22) | | |
| (23) | | |
| (24) | | |
| (25) | | |

TABLE 1-continued

| Compound of formula | R₁ | X₁ |
|---|---|---|
| (26) | (trisiloxane propyl ester group) | *—NH—CH₂CH₂—NH—* |
| (27) | (trisiloxane propyl ester group) | *—NH—CH(CH₃)CH₂—NH—* |
| (28) | (trisiloxane propyl ester group) | *—NH—CH₂—C(CH₃)₂—CH₂—NH—* |
| (29) | (trisiloxane propyl ester group) | *—NH—(CH₂)₇—NH—* |
| (30) | (trisiloxane propyl ester group) | isophorone diamine linker |
| (31) | (trisiloxane propyl ester group) | bis(methylcyclohexyl)methane diamine linker |
| (32) | (trisiloxane propyl ester group) | *—NH—(CH₂)₁₂—NH—* |

TABLE 1-continued

| Compound of formula | R₁ | X₁ |
|---|---|---|
| (33) | 3-(trimethylsiloxy)(trimethylsiloxy)methylsilylpropyl ester | *–NH–CH₂CH₂CH₂–O–CH₂CH₂CH₂CH₂–O–CH₂CH₂CH₂–NH–* |
| (34) | 3-(trimethylsiloxy)(trimethylsiloxy)methylsilylpropyl ester | *–NH–CH₂CH₂–N(Et)–* |
| (35) | 3-(trimethylsiloxy)(trimethylsiloxy)methylsilylpropyl ester | *–NH–CH₂CH₂CH₂–N(cyclohexyl)–* |
| (36) | 3-(trimethylsiloxy)(trimethylsiloxy)methylsilylpropyl ester | *–NH–CH₂CH₂CH₂–N(CH₃)–CH₂CH₂CH₂–NH–* |
| (37) | 3-(trimethylsiloxy)(trimethylsiloxy)methylsilylpropyl ester | *–NH–CH₂CH₂–NH–* |
| (38) | 3-(trimethylsiloxy)(trimethylsiloxy)methylsilylpropyl amide | *–NH–CH₂CH₂–NH–* |
| (39) | 3-(trimethylsiloxy)(trimethylsiloxy)methylsilylpropyl amide | *–NH–CH(CH₃)CH₂–NH–* |

TABLE 1-continued

Compound of formula (40)-(46): tetra-anilino triazine structures with R₁ substituents (propylamide-linked bis(trimethylsilyloxy)methylsilyl groups) and bridging X₁ diamine linkers:

- (40) X₁ = –NH–CH₂–C(CH₃)₂–CH₂–NH–
- (41) X₁ = –NH–(CH₂)₇–NH–
- (42) X₁ = isophorone diamine residue (3,3,5-trimethylcyclohexane with NH and CH₂NH)
- (43) X₁ = 4,4′-methylenebis(2-methylcyclohexylamine) residue
- (44) X₁ = –NH–(CH₂)₁₂–NH–
- (45) X₁ = –NH–(CH₂)₃–O–(CH₂)₄–O–(CH₂)₃–NH–
- (46) X₁ = –NH–CH₂CH₂–N(C₂H₅)–

TABLE 1-continued

| Compound of formula | R₁ | X₁ |
|---|---|---|
| (47) | *C(=O)NH-CH₂CH₂CH₂-Si(CH₃)(OSi(CH₃)₃)₂ | *NH-CH₂CH₂CH₂-N(cyclohexyl)-* |
| (48) | *C(=O)NH-CH₂CH₂CH₂-Si(CH₃)(OSi(CH₃)₃)₂ | *NH-CH₂CH₂CH₂-N(CH₃)-CH₂CH₂CH₂-NH-* |
| (49) | *C(=O)NH-CH₂CH₂CH₂-Si(CH₃)(OSi(CH₃)₃)₂ | *O-(CH₂)₆-O-* |
| (50) | *C(=O)O-CH₂CH₂CH₂-Si(CH₃)(OSi(CH₃)₃)₂ | *O-(CH₂)₅-O-* |
| (51) | *C(=O)O-CH₂CH(C₂H₅)(CH₂)₃CH₃ | *O-(CH₂)₆-O-* |
| (52) | *C(=O)O-CH₂CH(C₂H₅)(CH₂)₃CH₃ | *O-C(CH₃)₂-(CH₂)₃-C(CH₃)₂-O-* |
| (53) | *C(=O)O-CH₂CH(C₂H₅)(CH₂)₃CH₃ | *O-CH₂-C(CH₃)₂-CH₂-O-* |

TABLE 1-continued
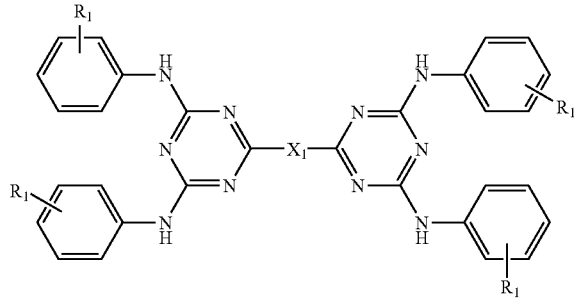
| Compound of formula | R₁ | X₁ |
|---|---|---|
| (54) | 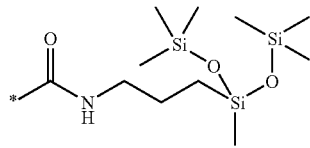 |  |
| (55) | —CO(O)—CH₃ | —NH—(CH₂)₂—NH— |
| (56) | 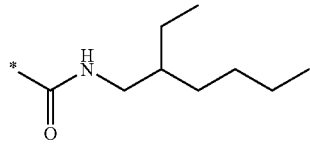 | 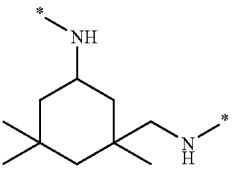 |
| (57) | 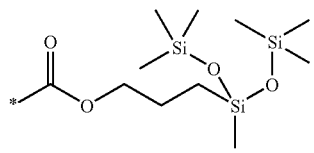 |  |
| (58) | 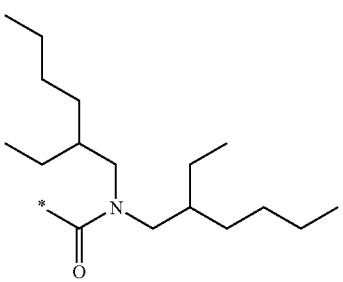 | 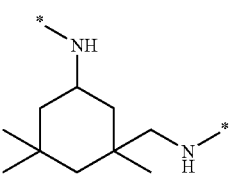 |
| (59) | 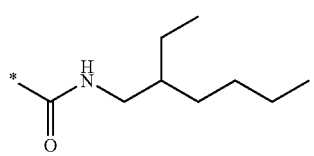 | 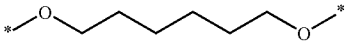 |
| (60) | 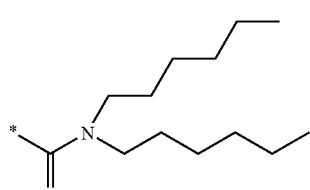 | 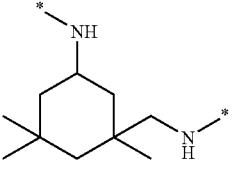 |

The compounds of formula (1) are prepared by methods known from the prior art, as disclosed for example in Journal of the Institution of Chemists (inida), 6 (5), p. 197 (1984); or in Journal of the Institution of Chemists (inida), 57 (6), p. 233 (1985); or in EP 818 450. The method generally comprises reacting 2 moles of a halogentriazine of formula (1m), preferably chlorotriazine, with 1 mole of the compound of formula (1n) to give the compound of formula (1) according to the following reaction scheme:

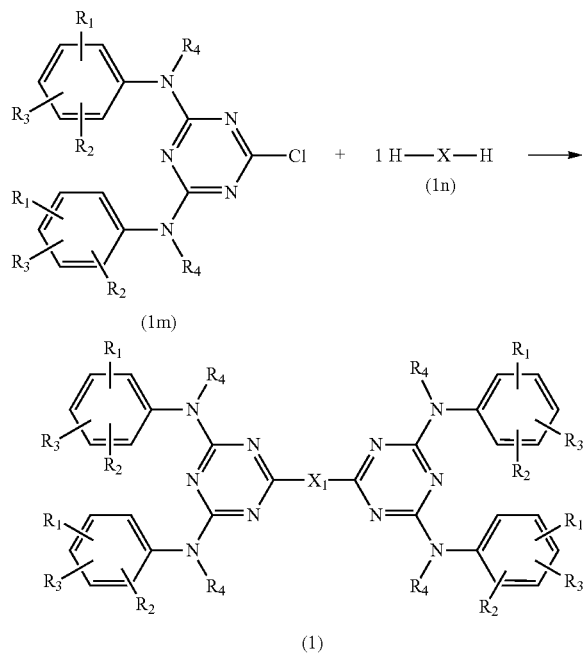

wherein
$R_1$, $R_2$, $R_3$, $R_4$ and $X_1$ are defined as in formula (1).

The reaction is preferably carried out in dipolar aprotic solvents, like dimethylfomamide, di-methylsulfoxide, sulfolane, N-methyl-pyrrolidone; hydrocarbons like xylene or toluene, tetra-line, petroleum, mesytilene or benzene; hydrogenated halocarbons like chlorobenzene or dichlorobenzene; or without a solvent using an excess of a base like tetraalylamines; or without any solvent and a base in a "melt process".

The reaction temperature is preferably from 20 to 280, preferably 30 to 200, and most preferably from 40 to 150° C.

Preferred bases used in the present process are trialkylamines like triethylamine, ethyl-iso-propylamine, heterocyclic amines like DABCO or DBU, or inorganic bases like $NH_2CO_3$ or $NaHCO_3$.

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations.

The UV absorbers of formula (1) according to the present invention, depending on the definition of $X_1$ and $R_1$ can be used either in the dissolved state (soluble organic filters, solubilized organic filters) or in the micronised state (nanoscalar organic filters, particulate organic filters, UV-absorber pigments).

Any known process suitable for the preparation of microparticles can be used for the preparation of the micronised UV absorbers, for example wet-milling, wet-kneading, spray-drying from a suitable solvent, by the expansion according to the RESS process (Rapid Expansion of Supercritical Solutions) by reprecipitation from suitable solvents.

The micronised UV absorbers so obtained usually have an average particle size from 0.02 to 2, preferably from 0.03 to 1.5, and more especially from 0.05 to 1.0 micrometer.

The process for the preparation of the micronized compound of formula (1) is another object of the present invention.

A further object of the present invention is a UV absorber dispersion, comprising
(a) a micronised UV absorber of formula (1), each of them having a particle size from 0.02 to 2 μm, and
(b) a suitable dispersing agent.

The cosmetic formulations or pharmaceutical compositions according to the present invention may additionally contain one or more than one further conventional UV filter.

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes: hydrocarbon oils: silicones or siloxanes, organosubstituted super-fatting agents, surfactants consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as spf enhancers.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

The cosmetic preparation according to the invention is distinguished by excellent protection of human skin against the damaging effect of sunlight.

A. PREPARATION EXAMPLES

Example A1

Preparation of the Compound of Formula

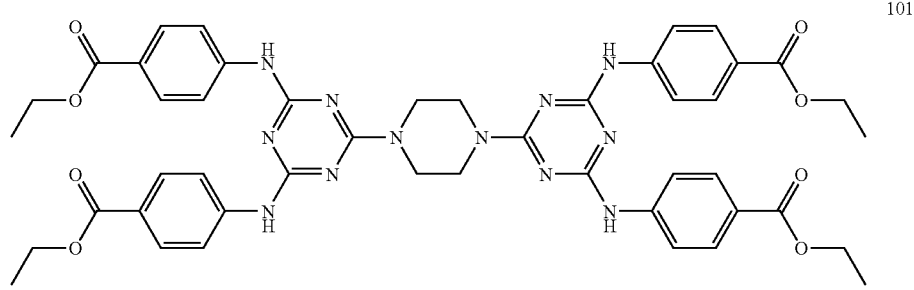 [SMILES: CCOC(=O)c1ccc(Nc2nc(Nc3ccc(C(=O)OCC)cc3)nc(N3CCN(c4nc(Nc5ccc(C(=O)OCC)cc5)nc(Nc5ccc(C(=O)OCC)cc5)n4)CC3)n2)cc1]

(101)

1.8 g (0.021 mol) piperazine are added to a solution of 4.4 g (0.01 mol) of the monochlorotriazine of formula

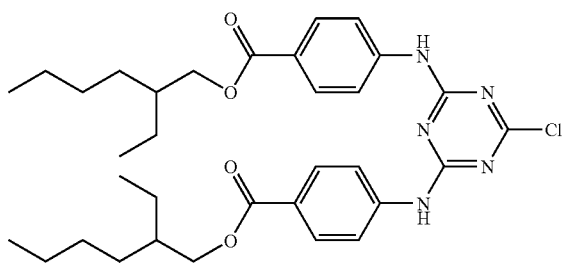

(101a)

in 50 ml dimethylformamide and stirred at 75° C. for 2 h.

The reaction solution is decanted on 100 ml water and stirred.

The raw product is filtered off, washed with water, stirred in aceton, filtered off and dried in vacuo at 80° C.

A white product is obtained.

Yield: 2.0 g (44.6%) colorless crystals; Fp=287-290° C.

NMR:

$^{13}$C NMR (90 MHz): δ=14.61 (CH$_3$), 60.63. (CH$_2$), 119.35 (CH), 122.99 (Cq), 130.35 (CH), 145.02 (Cq), 164.38 (Cq), 164.98 (Cq), 165.88 (Cq).

Example A2

Preparation of the Compound of Formula

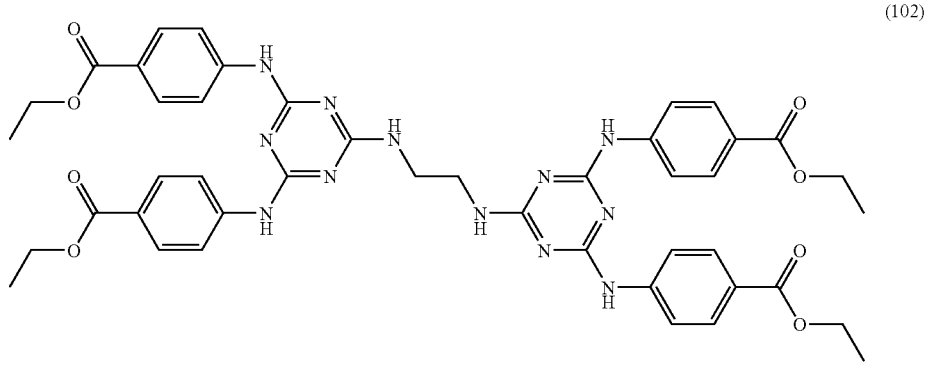 [SMILES: CCOC(=O)c1ccc(Nc2nc(NCCNc3nc(Nc4ccc(C(=O)OCC)cc4)nc(Nc4ccc(C(=O)OCC)cc4)n3)nc(Nc3ccc(C(=O)OCC)cc3)n2)cc1]

(102)

0.3 g ethylendiamine (0.005 mol) and 1.1 g triethylamine (0.011 mol) are added to a solution of 4.4 g (0.01 mol) of the monochlorotriazine of formula (101a) in 50 ml dimethylformamide and stirred for 2 h at 75° C.

The reaction solution concentrated with a rotary evaporator until drying, gathered in water and weakly acidified with hydrochloric acid (1N).

The raw product is filtered off and washed neutral.

After decocting in acetone a white product is obtained.

Yield: 2.7 g (62.0%); Fp=213-215° C.

$^{13}$C NMR (90 MHz): δ=14.55 (CH$_3$), 14.58 (CH$_3$), 60.52 (CH$_2$), 60.55 (CH$_2$), 119.20 (CH), 122.73 (CH), 122.82 (CH), 130.15 (CH), 145.13 (Cq), 145.29 (Cq), 164.22 (Cq), 164.41 (Cq), 165.87 (Cq), 166.16 (Cq).

Example A3

Preparation of the Compound of Formula

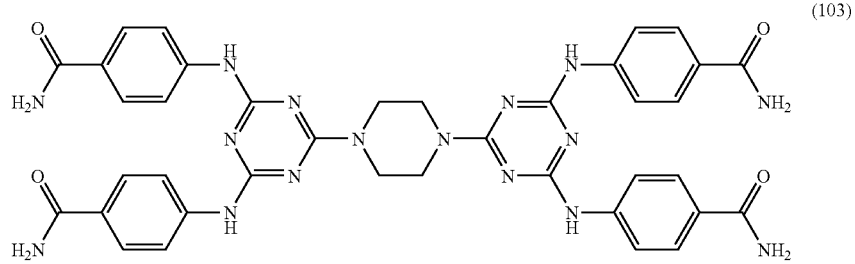 [SMILES: NC(=O)c1ccc(Nc2nc(Nc3ccc(C(N)=O)cc3)nc(N3CCN(c4nc(Nc5ccc(C(N)=O)cc5)nc(Nc5ccc(C(N)=O)cc5)n4)CC3)n2)cc1]

(103)

A solution of 34.7 g (0.255 mol) 4-aminobenzamide in 100 ml methyl-2-pyrrolidone is added to a solution of 46.1 g cyanuric chloride (0.25 mol) in a 800 ml dioxan/water mixture (9:1) at 5° C. and a pH of 3.5.

Then a solution of 34.7 g 4-aminobenzamide (0.255 mol) in 100 ml methylpyrrolidone is added at 60-90° C. and pH of 8.5.

The suspension is diluted at 60° C., filtered off warm and washed with dioxan and water.

After decocting with in dimethylfomamide and acetone a white product of formula

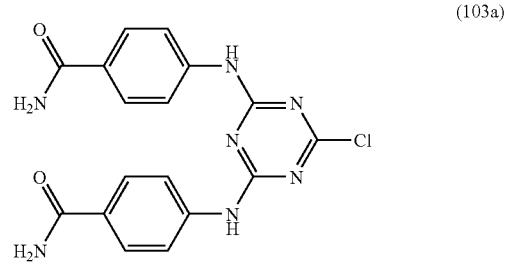 [SMILES: NC(=O)c1ccc(Nc2nc(Cl)nc(Nc3ccc(C(N)=O)cc3)n2)cc1]

(103a)

is obtained.

0.432 g (0.005 mol) piperazine and 1.1 g triethylamine (0.01 mol) are added to a solution of 3.84 g (0.01 mol) of the monochlorotriazine of formula (103a) in dimethylfomamide.

The reaction mixture is stirred at 75° C. for 6 h and then at 90° C. for 1 h.

After concentrating with the rotary evaporator until drying the residue is gathered in water, weakly acidified with hydrochloric acid, filtered off and washed neutral with water.

After recrystallization from 1-methyl-2-pyrrolidone and decocting in methanol a white product is obtained.

Yield: 1.95 g (49.9%)

Melting point: decomposition starting at 260° C.

Elemental analysis of the compound of formula (103:

|  | C | H | N |
|---|---|---|---|
| Calculated | 58.45 | 4.65 | 28.70 |
| Found | 58.07 | 4.93 | 28.13 |

Example A4

Preparation of the Compound of Formula

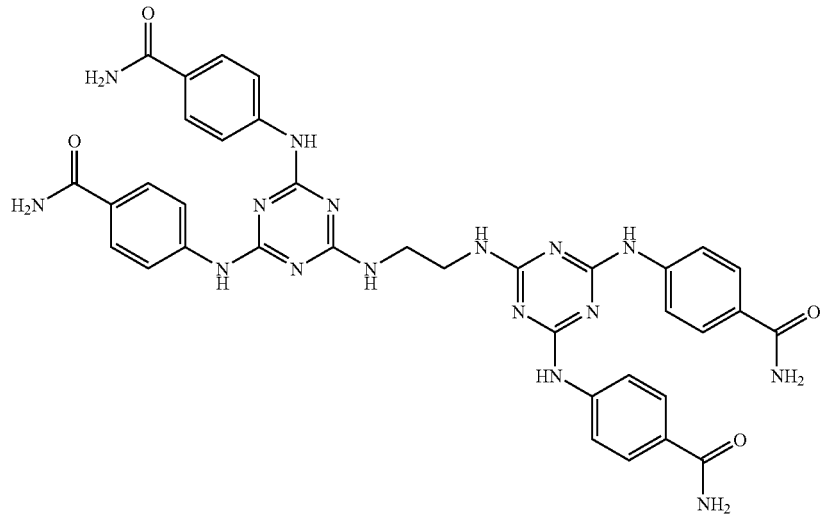

(104)

0.30 g (0.005 mol) ethylenediamine and 1.1 g triethylamine (0.01 mol) are added to a solution of 3.84 g (0.01 mol) of the monochlorotriazine of formula (103a) in 50 ml dimethylformamide and stirred for 5.5 h at 75° C.

The clear solution is concentrated with a rotary evaporator until drying, gathered in water, weakly acidified with hydrochloric acid, filtered off and washed neutral with water.

After recrystallization from a dimethylformamide/water mixture (4:6) and decocting in acetone a white product is obtained.

Yield: 0.8 g (21.2%)

NMR:

$^{13}$C NMR (90 MHz): δ=31.14, 36.14, 119.26 (CH), 127.72 (Cq), 128.51 (CH), 128.69, 143.09 (Cq), 162.70 (Cq), 163.35 (CH), 163.90 (Cq), 165.13 (Cq), 168.03 (Cq).

Example A5

Preparation of the Compound of Formula

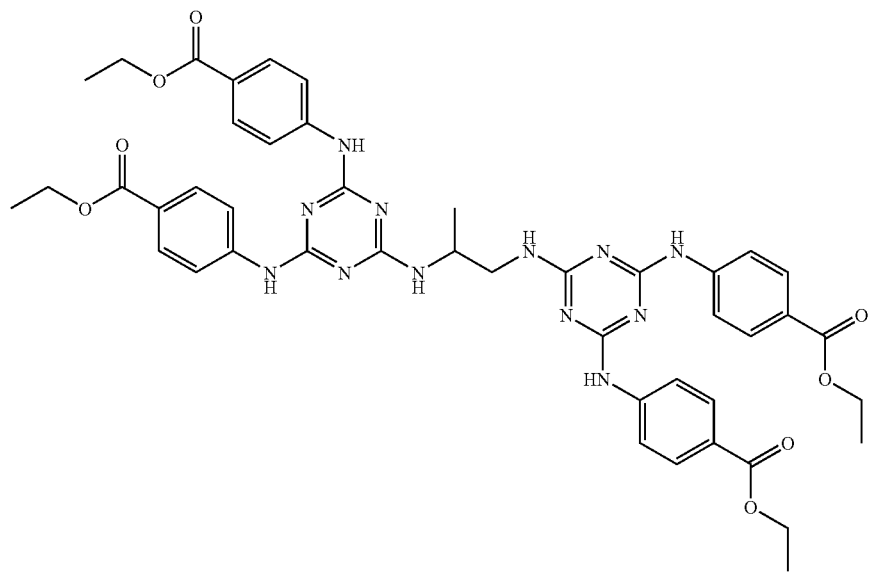

0.37 g (0.005 mol) propylenediamine and 1.1 g (0.01 mol) triethylamine are added to a solution of 4.4 g (0.01 mol) of the monochlorotriazine of formula (101a) in 50 ml dimethylformamide and stirred for 4 h at 75° C.

After concentrating with the rotary evaporator until drying the residue is gathered in water and filtered off.

After dissolving in tert. butylmethylether the organic phase is shaken out with brine solution (5%), dried over sodium sulfate and concentrated until drying.

A white product is obtained by column chromatographic purification.

Yield: 2.3 g (52%)

NMR:

$^{13}$C NMR (90 MHz): δ=14.53 (CH$_3$), 14.58 (CH$_3$), 19.04 (CH$_3$), 46.03. (CH$_2$), 46.68. (CH), 60.54 (CH$_2$), 119.22 (CH), 122.73 (Cq), 122.85 (Cq), 130.13 (CH), 145.11 (Cq), 145.25 (Cq), 145.32 (Cq), 164.25 (Cq), 164.38 (Cq), 165.75 (Cq), 165.84 (Cq), 165.87 (Cq), 166.26 (Cq).

Example A6

The compound of formula (5) (Table 1) is prepared according to the method as described in Example 1. Piperazine is replaced by p-phenylene-diamine.

Example A7

The compound of formula (18) (Table 1) is prepared according to the method as described in Example 1. Piperazine is replaced by isophoron-diamine (CAS No. 2855-13-2). The compound of formula (101a) is replaced by (105)

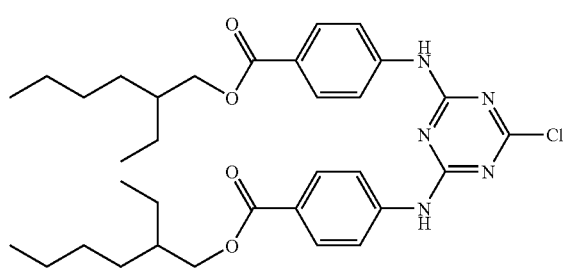 [SMILES: CCCCC(CC)COC(=O)c1ccc(Nc2nc(Cl)nc(Nc3ccc(C(=O)OCC(CC)CCCC)cc3)n2)cc1]

Example A8

The compound of formula (19) (Table 1) is prepared according to the method as described in Example 1. Piperazine is replaced by 4,4'-diamino-3,3'-dimethyldicyclohexylmethane. The compound of formula (101a) is replaced by

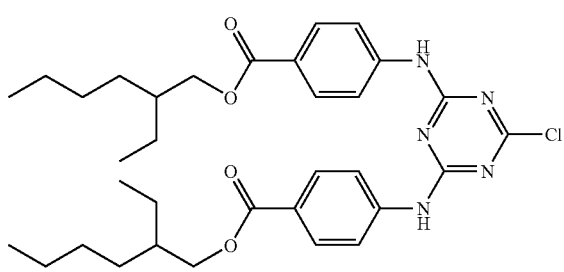 [SMILES: CCCCC(CC)COC(=O)c1ccc(Nc2nc(Cl)nc(Nc3ccc(C(=O)OCC(CC)CCCC)cc3)n2)cc1]

Example A9

The compound of formula (20) (Table 1) is prepared according to the method as described in Example 1. Piperazine is replaced by dodecane-1,12-diamine. The compound of formula (101a) is replaced by

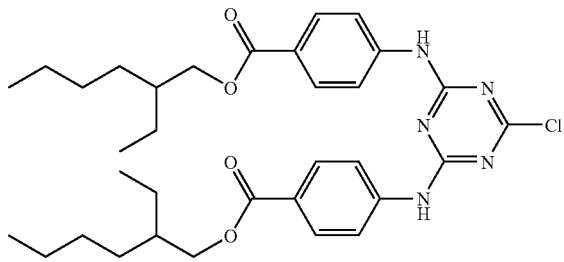 [SMILES: CCCCC(CC)COC(=O)c1ccc(Nc2nc(Cl)nc(Nc3ccc(C(=O)OCC(CC)CCCC)cc3)n2)cc1]

Example A10

The compound of formula (30) (Table 1) is prepared according to the method as described in Example 1. Piperazine is replaced by isophoron-diamine. The compound of formula (101a) is replaced by

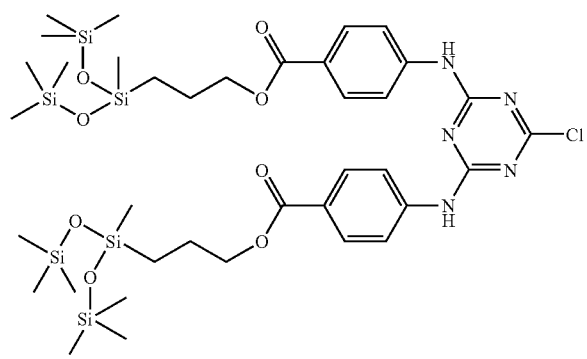 [SMILES: C[Si](C)(C)O[Si](C)(CCCOC(=O)c1ccc(Nc2nc(Cl)nc(Nc3ccc(C(=O)OCCC[Si](C)(O[Si](C)(C)C)O[Si](C)(C)C)cc3)n2)cc1)O[Si](C)(C)C]

Example A11

The compound of formula (32) (Table 1) is prepared according to the method as described in Example 1. Piperazine is replaced by dodecane-1,12-diamine. The compound of formula (101a) is replaced by

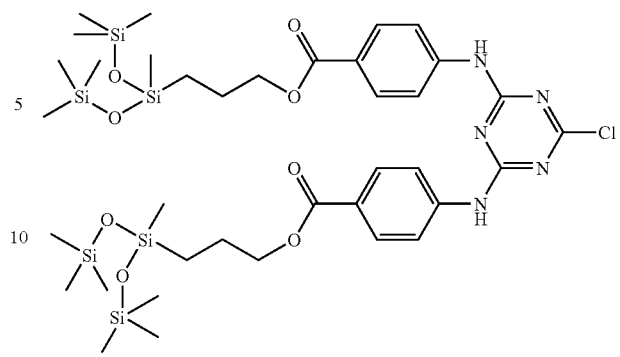

Example A12

The compound of formula (43) (Table 1) is prepared according to the method as described in Example 1. Piperazine is replaced by 4,4'-diamino-3,3'-dimethyldicyclohexyl-methane The compound of formula (101a) is replaced by

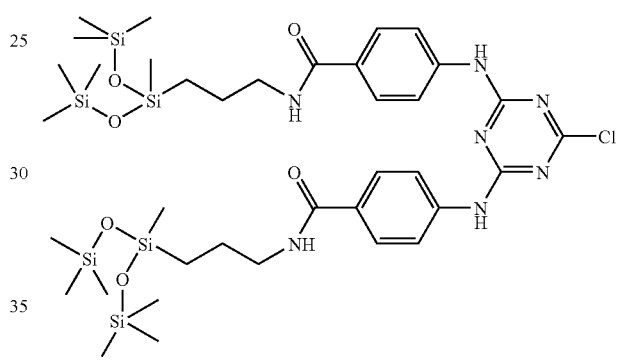

Example A13

The compound of formula (31) (Table 1) is prepared according to the method as described in Example 1. Piperazine is replaced by 4,4'-Diamino-3,3'-dimethyldicyclohexyl-methane. The compound of formula (101a) is replaced by

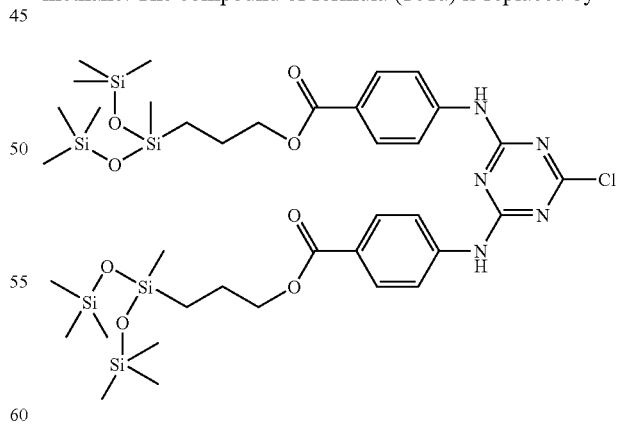

Example A14

The compound of formula (51) (Table 1) is prepared according to the method as described in Example 1. Piperazine is replaced by 1,6-hexandiol. The compound of formula (101a) is replaced by

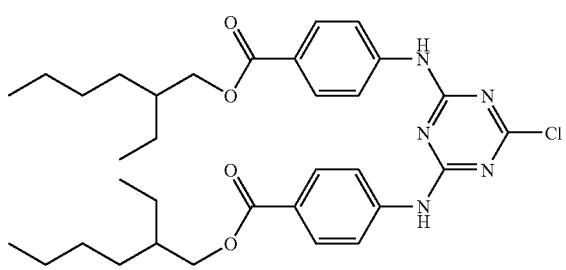 [SMILES: CCCCC(CC)COC(=O)c1ccc(Nc2nc(Cl)nc(Nc3ccc(C(=O)OCC(CC)CCCC)cc3)n2)cc1]

Example A15

The compound of formula (53) (Table 1) is prepared according to the method as described in Example 1. Piperazine is replaced by neopentylglycol (CAS No. 126-30-7). The compound of formula (101a) is replaced by

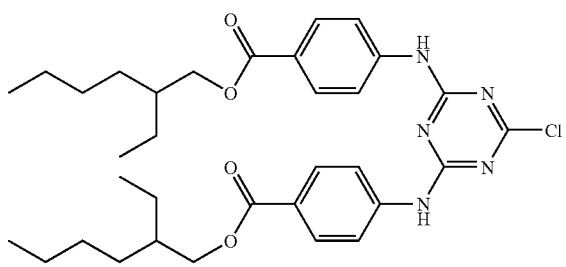 [SMILES: CCCCC(CC)COC(=O)c1ccc(Nc2nc(Cl)nc(Nc3ccc(C(=O)OCC(CC)CCCC)cc3)n2)cc1]

Example A16

The compound of formula (57) (Table 1) is prepared according to the method as described in Example 1. Piperazine is replaced by neopentylglycol. The compound of formula (101a) is replaced by

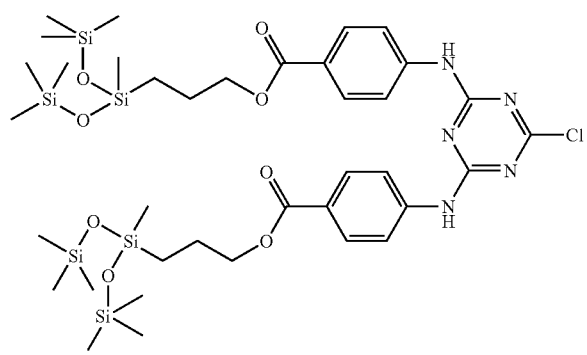 [SMILES: C[Si](C)(C)O[Si](C)(CCCOC(=O)c1ccc(Nc2nc(Cl)nc(Nc3ccc(C(=O)OCCC[Si](C)(O[Si](C)(C)C)O[Si](C)(C)C)cc3)n2)cc1)O[Si](C)(C)C]

Example A17

The compound of formula (50) (Table 1) is prepared according to the method as described in Example 1. Piperazine is replaced by 1,6-hexandiol. The compound of formula (101a) is replaced by

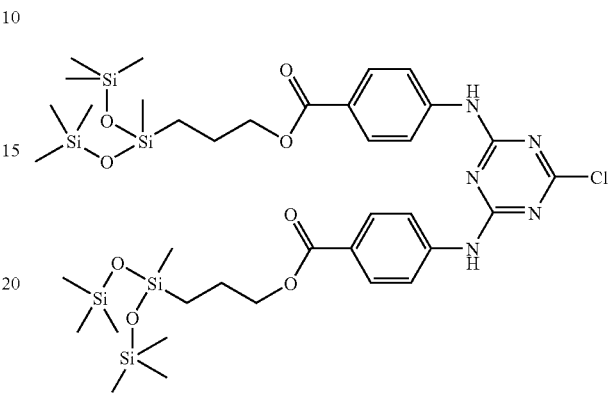

Example A18

The compound of formula (49) (Table 1) is prepared according to the method as described in Example 1. Piperazine is replaced by 1,6-hexandiol. The compound of formula (101a) is replaced by

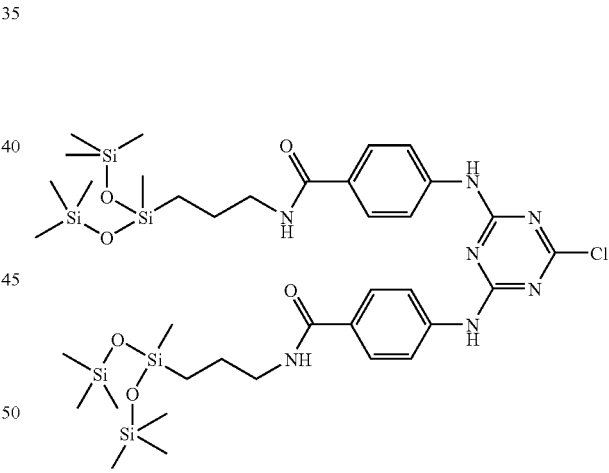

B. Application Examples

| INCI-Name | A % w/w | B % w/w | C % w/w | D % w/w | E % w/w | F % w/w | G % w/w |
|---|---|---|---|---|---|---|---|
| Example B1: | | | | | | | |
| Ethylhexyl Methoxycinnnamate | 9.8 | 9.8 | 9.8 | 9.8 | 9.8 | 9.8 | 9.8 |
| Cyclomethicone | 7.0 | 7.0 | 7.0 | 7.0 | 7.0 | 7.0 | 7.0 |
| Octadecene/MA Copolymer (and) Methyl Acethyl Ricinoleate (and) Di-methylhepthyl Adipate | | 3.0 | | | | | |

-continued

| INCI-Name | A % w/w | B % w/w | C % w/w | D % w/w | E % w/w | F % w/w | G % w/w |
|---|---|---|---|---|---|---|---|
| C30-38 olefin/isopropyl maleate/MA copolymer | | | 2.0 | | | | |
| Hydrogenated Dimer Dilinoleyl/Dimethylcarbonate Copolymer | | | | 3.0 | | | |
| Cyclopentasiloxane (and) Acrylates/Polytrimethylsiloxymethacrylate Copolymer | | | | | | 7.0 | |
| Isododecane (and) Acrylates/Polytrimethylsiloxymethacrylate Copolymer | | | | | | 8.0 | |
| Poly(Glycol Adipate)/Bis-Hydroxyethyoxypropyl Dimethicone Copolymer | | | | | | | 5.0 |
| Ethylhexyl Palmitate | 5.0 | 5.0 | 5.0 | 5.0 | 5.0 | 5.0 | 5.0 |
| Bis-Ethylhexyloxyphenol Methoxyphenyl Triazine | 2.0 | 2.0 | 2.0 | 2.0 | 2.0 | 2.0 | 2.0 |
| Pentaerythrityl Distearate | | 1.5 | | | | | 3.0 |
| Glyceryl Dibehenate (and) Tribehenin (and) Glyceryl Behenate | | | | 2.0 | 4.0 | | |
| Glyceryl Stearate | 1.5 | | | 1.5 | | 1.5 | |
| C20-22 Alkyl Phosphate (and) C20-22 Alcohols | | 3.0 | | | | 2.5 | |
| Candelilla/Jojoba/Rice Bran Polyglyceryl-3 esters (and) glyceryl stearate (and) Cetearyl alcohol (and) Sodium stearoyl lactylate | | | 6.0 | | | | 4.0 |
| Glyceryl oleate citrate (and) Caprylic/Capric Triglycerides | | | | 5.0 | | | |
| Potassium Cetyl Phosphate | 1.8 | | | | 1.8 | | |
| VP/Eicosene Copolymer | 0.6 | | | | 0.6 | | |
| Aqua | Qs to 100 | Qs to 100 | Qs to 100 | Qs to 100 | Qs to 100 | Qs to 100 | Qs to 100 |
| Methylene Bis-Benzotriazolyl Tetramethylbutylphenol | 2.0 | 2.0 | 2.0 | 2.0 | 2.0 | 2.0 | 2.0 |
| PVP/dimethylconylacrylate/polycarbamyl/polyglycol ester | | | | | | | |
| Polyester-5 | | | | | | | |
| Acrylates/Palmeth-25 Acrylate Copolymer | 0.3 | | | | | | |
| Distearetyh-75 IPDI | | 0.3 | 3.0 | | | | |
| Distearetyh-100 IPDI | | | | 0.3 | 3.0 | | |
| Acrylates/Vinyl Neodecanoate Crosspolymer | | | | | | 1.5 | 5.0 |
| Compound of formula (56) or (3) or (12) or (17) or (18) or (19) or (20) or (24) or (30) or (31) or (32) or (35) or (41) or (42) or (43) or (44) or (50) or (51) or (53) | 2.0 | 4.0 | 6.0 | 8.0 | 10.0 | 12.0 | 14.0 |
| Micronized 2,4,6-Tris(p-biphenylyl)-s-triazine [CAS No. 31274-51-8] | 5.0 | 9.0 | 3.0 | 1.0 | 7.0 | 2.0 | 15.0 |
| Glycerin | 6.0 | 6.0 | 6.0 | 6.0 | 6.0 | 6.0 | 6.0 |
| Disodium EDTA | 0.2 | 0.2 | 0.2 | 0.2 | 0.2 | 0.2 | 0.2 |
| Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 |
| Tocopheryl Acetate | 0.3 | 0.3 | 0.3 | 0.3 | 0.3 | 0.3 | 0.3 |
| Example B2 | | | | | | | |
| C12-15 Alkyl Benzoate | 4.0 | 4.0 | 4.0 | 4.0 | 4.0 | 4.0 | 4.0 |
| Butyl Methoxydibenzoylmethane | 1.0 | 1.0 | 1.0 | 1.0 | 1.0 | 1.0 | 1.0 |
| Octocrylene | 7.5 | 7.5 | 7.5 | 7.5 | 7.5 | 7.5 | 7.5 |
| Isohexadecane | 3.0 | 3.0 | 3.0 | 3.0 | 3.0 | 3.0 | 3.0 |
| Cyclopentasiloxane | 4.0 | 4.0 | 4.0 | 4.0 | 4.0 | 4.0 | 4.0 |
| Terephthalylidene Dicamphor Sulfonic Acid | 0.3 | 0.3 | 0.3 | 0.3 | 0.3 | 0.3 | 0.3 |
| Titanium Dioxide particles size 10 to 100 nm | 1.7 | 1.7 | 1.7 | 1.7 | 1.7 | 1.7 | 1.7 |
| TiO2 (and) isodeceth-6(and)Oleth-10(and)Alumina(and) Simethicone | | 1.5 | | | | | 1.0 |
| Alumina coated TiO2 | | | 2.0 | | 4.0 | | |
| TiO2(and)isolaureth-4 Phosphate(and)Vinylbuteth-25/Sodium maleate copolymer | 0.5 | 0.5 | 0.5 | 0.5 | 0.5 | 0.5 | 0.5 |
| TiO2(and)Diethylhexylcarbonate(and)polyglyceryl-6 polyhydroxystearate | 0.8 | 0.8 | 0.8 | 0.8 | 0.8 | 0.8 | 0.8 |
| TiO2(and)Aluminum hydroxide(and)Dimethiconol methicone copolymer | | 3.0 | | | | | |
| TiO2(and)Aluminum hydroxide(and)Dimethiconol methicone copolymer | | | 2.0 | | | | |
| Silica coated TiO2 | | | | 3.0 | | | |
| TiO2(and)Aluminium hydroxide(and) Isostearic acid | | | | | 7.0 | | |
| Maganese modified TiO2 | | | | | | 8.0 | |
| ZnO particles size 10 to 100 nm | 3.0 | 3.0 | 3.0 | 3.0 | 3.0 | 3.0 | 3.0 |
| Pentaerythrityl Distearate | | 1.5 | | | | | 1.0 |
| Glyceryl Dibehenate (and) Tribehenin (and) Glyceryl Behenate | | | 2.0 | | 4.0 | | |
| Stearic Acid | 0.5 | 0.5 | 0.5 | 0.5 | 0.5 | 0.5 | 0.5 |
| PEG-100 Stearate (and) Glyceryl Stearate | 0.8 | 0.8 | 0.8 | 0.8 | 0.8 | 0.8 | 0.8 |

| INCI-Name | A % w/w | B % w/w | C % w/w | D % w/w | E % w/w | F % w/w | G % w/w |
|---|---|---|---|---|---|---|---|
| Octadecene/MA Copolymer (and) Methyl Acethyl Ricinoleate (and) Di-methylhepthyl Adipate | | 3.0 | | | | | |
| C30-38 olefin/isopropyl maleate/MA copolymer | | | 2.0 | | | | |
| Hydrogenated Dimer Dilinoleyl/Dimethylcarbonate Copolymer | | | | 3.0 | | | |
| Cyclopentasiloxane (and) Acrylates/Polytrimethylsiloxymethacrylate Copolymer | | | | | 7.0 | | |
| Isododecane (and) Acrylates/Polytrimethylsiloxymethacrylate Copolymer | | | | | | 8.0 | |
| Poly(Glycol Adipate)/Bis-Hydroxyethyoxypropyl Dimethicone Copolymer | | | | | | | 5.0 |
| C20-22 Alkyl Phosphate (and) C20-22 Alcohols | | 2.5 | | | | 3.0 | |
| Candelilla/Jojoba/Rice Bran Polyglyceryl-3 esters (and) glyceryl stearate (and) Cetearyl alcohol (and) Sodium stearoyl lactylate | | | 5.0 | | | | 6.0 |
| Glyceryl oleate citrate (and) Caprylic/Capric Triglycerides | | | | 4.0 | | | |
| Potassium Cetyl Phosphate | 1.3 | | | | 1.3 | | |
| PVP/Eicosene Copolymer | 1.0 | | | | | | |
| Aqua | Qs to 100 | Qs to 100 | Qs to 100 | Qs to 100 | Qs to 100 | Qs to 100 | Qs to 100 |
| Glycerin | 4.0 | 4.0 | 4.0 | 4.0 | 4.0 | 4.0 | 4.0 |
| Compound of formula (56) or (3) or (12) or (17) or (18) or (19) or (20) or (24) or (30) or (31) or (32) or (35) or (41) or (42) or (43) or (44) or (50) or (51) or (53) | 2.0 | 4.0 | 6.0 | 8.0 | 10.0 | 12.0 | 14.0 |
| Micronized 2,4,6-Tris(p-biphenylyl)-s-triazine [CAS No. 31274-51-8] | 5.0 | 9.0 | 3.0 | 1.0 | 7.0 | 2.0 | 15.0 |
| Propylene Glycol | 5.0 | 5.0 | 5.0 | 5.0 | 5.0 | 5.0 | 5.0 |
| Xanthan Gum | 0.2 | 0.2 | 0.2 | 0.2 | 0.2 | 0.2 | 0.2 |
| PVP/dimethylconylacrylate/polycarbamyl/polyglycol ester Polyester-5 | | | | | | | |
| Disteareth-75 IPDI | | 0.3 | 3.0 | | | | |
| Disteareth-100 IPDI | | | | 0.3 | 3.0 | | |
| Acrylates/Vinyl Neodecanoate Crosspolymer | | | | | | 1.5 | 5.0 |
| Acrylates/C10-30 Alkyl Acrylate Crosspolymer | 0.2 | | | | | | |
| Disodium EDTA | 0.2 | 0.2 | 0.2 | 0.2 | 0.2 | 0.2 | 0.2 |
| Triethanolamine | Qs | Qs | Qs | Qs | Qs | Qs | Qs |
| Dimethicone | 0.4 | 0.4 | 0.4 | 0.4 | 0.4 | 0.4 | 0.4 |
| Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 |
| Tocopheryl Acetate | 0.9 | 0.9 | 0.9 | 0.9 | 0.9 | 0.9 | 0.9 |
| Example B3 | | | | | | | |
| Synthetic Beeswax | 0.5 | 0.5 | 0.5 | 0.5 | 0.5 | 0.5 | 0.5 |
| Ethylhexyl Methoxycinnamate (stabilized by incorporating into a polymer) | 9.8 | 9.8 | 9.8 | 9.8 | 9.8 | 9.8 | 9.8 |
| Isoamyl p-Methoxycinnamate | 2.0 | 2.0 | 2.0 | 2.0 | 2.0 | 2.0 | 2.0 |
| Ethylhexyl Salicylate | 5.0 | 5.0 | 5.0 | 5.0 | 5.0 | 5.0 | 5.0 |
| Butyl Methoxydibenzoylmethane (stabilized by incorporating into a polymer) | 4.0 | 4.0 | 5.0 | 4.0 | 4.0 | 4.0 | 3.0 |
| 4-Methylbenzylidene Camphor | 4.0 | 4.0 | 4.0 | 4.0 | 4.0 | 4.0 | 4.0 |
| Bis-Ethylhexyloxyphenol Methoxyphenyl Triazine | 2.0 | 3.0 | 2.0 | 1.0 | 1.0 | 1.0 | 1.0 |
| Octadecene/MA Copolymer (and) Methyl Acethyl Ricinoleate (and) Di-methylhepthyl Adipate | | 3.0 | | | | | |
| C30-38 olefin/isopropyl maleate/MA copolymer | | | 2.0 | | | | |
| Hydrogenated Dimer Dilinoleyl/Dimethylcarbonate Copolymer | | | | 3.0 | | | |
| Cyclopentasiloxane (and) Acrylates/Polytrimethyl-siloxymethacrylate Copolymer | | | | | 7.0 | | |
| Isododecane (and) Acrylates/Polytrimethylsiloxy-methacrylate Copolymer | | | | | | 8.0 | |
| Poly(Glycol Adipate)/Bis-Hydroxyethyoxypropyl Dimethicone Copolymer | | | | | | | 5.0 |
| Dimethicone | 4.5 | 4.5 | 4.5 | 4.5 | 4.5 | 4.5 | 4.5 |
| C20-22 Alkyl Phosphate (and) C20-22 Alcohols | | 3.0 | | | | 3.0 | |
| Candelilla/Jojoba/Rice Bran Polyglyceryl-3 esters (and) glyceryl stearate (and) Cetearyl alcohol (and) Sodium stearoyl lactylate | | | 4.0 | | | | 4.0 |
| Glyceryl oleate citrate (and) Caprylic/Capric Triglycerides | | | | 6.0 | | | |
| Cetearyl Alcohol (and) Dicetyl Phosphate (and) Ceteth-10 Phosphate | 4.5 | | | | 4.5 | | |
| Cetyl Ricinoleate | 3.0 | 3.0 | 3.0 | 3.0 | 3.0 | 3.0 | 3.0 |

-continued

| INCI-Name | A % w/w | B % w/w | C % w/w | D % w/w | E % w/w | F % w/w | G % w/w |
|---|---|---|---|---|---|---|---|
| Pentaerythrityl Distearate | | 1.5 | | | | | 3.0 |
| Glyceryl Dibehenate (and) Tribehenin (and) Glyceryl Behenate | | | 2.0 | | 4.0 | | |
| Hydroxypropyl Dimethicone Behenate | 2.2 | 1.0 | | 2.2 | 1.0 | 2.2 | 0.5 |
| Decyl Cocoate | 1.0 | 1.0 | 1.0 | 1.0 | 1.0 | 1.0 | 1.0 |
| Aqua | Qs to 100 | Qs to 100 | Qs to 100 | Qs to 100 | Qs to 100 | Qs to 100 | Qs to 100 |
| Propylene Glycol | 3.0 | 3.0 | 3.0 | 3.0 | 3.0 | 3.0 | 3.0 |
| Compound of formula (56) or (3) or (12) or (17) or (18) or (19) or (20) or (24) or (30) or (31) or (32) or (35) or (41) or (42) or (43) or (44) or (50) or (51) or (53) | 3.0 | 3.0 | 3.0 | 3.0 | 3.0 | 3.0 | 3.0 |
| 1,1'-(1,4-piperazinediyl)bis[1-[2-[4-(diethylamino)-2-hydroxybenzoyl]phenyl]-methanone (CAS No. 919803-06-8) | 2.0 | 3.0 | 1.0 | 8.0 | 4.0 | 3.0 | 1.0 |
| Decyl Glucoside | 0.5 | 0.5 | 0.5 | 0.5 | 0.5 | 0.5 | 0.5 |
| Acrylates/Vinyl Neodecanoate Crosspolymer | | | | | | | |
| Ammonium Acryloyldimethyltaurate/VP Copolymer | 0.3 | 0.3 | 0.3 | 0.3 | 0.3 | 0.3 | 0.3 |
| PVP/dimethylconylacrylate/polycarbamyl/polyglycol ester Polyester-5 | | | | | | | |
| Phenylbenzimidazole Sulfonic Acid | 2.0 | 2.0 | 2.0 | 2.0 | 2.0 | 2.0 | 2.0 |
| Disteareth-75 IPDI | | 0.3 | 3.0 | | | | |
| Disteareth-100 IPDI | | | | 0.3 | 3.0 | | |
| Acrylates/Vinyl Neodecanoate Crosspolymer | | | | | | 1.5 | 5.0 |
| Acrylates/C10-30 Alkyl Acrylate Crosspolymer | 0.2 | | | | | | |
| Disodium EDTA | 0.2 | 0.2 | 0.2 | 0.2 | 0.2 | 0.2 | 0.2 |
| Methylene Bis-Benzotriazolyl Tetramethylbutylphenol | 5.0 | 5.0 | 5.0 | 5.0 | 5.0 | 5.0 | 5.0 |
| Tromethamine | 0.8 | 0.8 | 0.8 | 0.8 | 0.8 | 0.8 | 0.8 |
| Cyclohexasiloxane (and) Cyclopentasiloxane | 0.8 | 0.8 | 0.8 | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 | 0.8 | 0.8 | 0.8 |
| Tocopheryl Acetate | 0.4 | 0.4 | 0.4 | 0.4 | 0.4 | 0.4 | 0.4 |
| CAS-Regno. 88122-99-0, Ethylhexyl triazone (Octyl triazone; Uvinul T 150) | 2.0 | 1.5 | 2.0 | | 1.0 | | |
| CAS-Regno. 6197-30-4, Octocrylene | 3.0 | 4.0 | 5.0 | | | 1.0 | 5.0 |
| CAS-Regno. 180898-37-7, Disodium phenyldibenzimidazoletetrasulfonate Neo Heliopan AP or Neo-Heliopan APC | 3.0 | 4.0 | 5.0 | 3.0 | | | |
| CAS-Regno. 302776-68-7, Uvinul A Plus | 4.0 | | 5.0 | | | | |
| CAS-Regno. 444811-29-4, Propanedioic acid, [(4-hydroxy-3,5-dimethoxyphenyl)methylene]-, bis(2-ethylhexyl) ester (Oxynex ST) | 3.0 | | 1.0 | | | | |
| CAS-Regno. 477844-93-2, Octofluorene | | 3.0 | 1.0 | | | | |
| 2-phenylethylbenzoate | | 1.0 | 1.0 | | | | |
| CAS-Regno. 68890-66-4, Octopirox | 2.0 | | | 3.0 | 1.0 | | |
| Tinogard TT (INCI Tetradibutyl Pentaerithrityl Hydroxy-hydrocinnamate) | 1.0 | | 1.0 | 1.0 | 3.0 | | |
| Tinogard HS (INCI Sodium Benzotriazolyl Butylphenol Sulfonate) | | 2.0 | 3.0 | | | 3.0 | |
| Tinogard TL (INCI Benzotriazolyl Dodecyl p-Cresol) | 2.0 | | 1.0 | 1.0 | | 1.0 | 3.0 |
| Phenol, 2-(2H-benzotriazol-2-yl)-6-dodecyl-4-methyl-, branched and linear | | 2.0 | | | 3.0 | | |
| Cibafast H Liquid (INCI Sodium Benzotriazolyl Butylphenol Sulfonate, Buteth-3, Tributyl Citrate) | 1.0 | | | | | | |
| Tinogard AS (INCI Bumetrizole) | 2.0 | | 1.0 | | | | |
| Tris(tetramethylhydroxypiperidinol) citrate (Tinogard Q) | 1.0 | | 1.0 | | | | |
| 220410-74-2 4-Piperidinol, 1-hydroxy-2,2,6,6-tetramethyl-, 2-hydroxy-1,2,3-propanetricarboxylate (3:1) (salt) | | | 1.0 | | | | 1.0 |
| CAS-Regno. 1750-49-8, N-(2-Hydroxypropyl)urea | | 5.0 | | | | 10.0 | |
| CAS-Regno. 2078-71-9, N-(2-Hydroxyethyl)urea | | | 10.0 | | 10.0 | | |
| mixture of n-butylphthalimide and isopropylphthalimide | 0.5 | | | 5.0 | | | |
| CAS-Regno. 872424-70-9 | 2.0 | | | | 1.0 | | |
| CAS-Regno. 872424-71-0 | | 2.0 | | | | 1.0 | |
| CAS-Regno. 872424-72-1 | | | 2.0 | | | | 1.0 |
| CAS-Regno. 872424-73-2 | | | | 2.0 | | | |
| mixture of glycosylglycerides or 2-O-beta-glucopyranosyl-sn-glycerin | 3.0 | | | | 2.0 | | |
| diaminobenzimidazole | 0.1 | | | | | | |
| dihydroxyacetone | | 2.0 | 4.0 | 2.0 | | | 2.0 |
| carnitine | 3.0 | 1.0 | | | | 1.0 | |
| Tropolone | 0.3 | | | | 0.2 | | |

| INCI-Name | A % w/w | B % w/w | C % w/w | D % w/w | E % w/w | F % w/w | G % w/w |
|---|---|---|---|---|---|---|---|
| CAS-Regno. 130603-71-3, alpha-Glucosylrutin | 0.5 | 0.1 | | 1.0 | | | |
| CAS-Regno. 425371-14-8 | | | | | | | |
| CAS-Regno. 425371-15-9 | | | | | | | |
| CAS-Regno. 261356-13-2 | | | | | | | 2.0 |
| CAS-Regno. 425371-03-5 | | | | | | 2.0 | |
| CAS-Regno. 425371-04-6 | | | | | 2.0 | | |
| CAS-Regno. 25371-05-7 | | | | 2.0 | | | |
| CAS-Regno. 425371-06-8 | | | | | 2.0 | | |
| CAS-Regno. 425371-07-9 | | | | | | | 2.0 |
| CAS-Regno. 425371-08-0 | | | | | | | |
| CAS-Regno. 425371-09-1 | | | | | | | |
| CAS-Regno. 425371-10-4 | | | | | | | |
| CAS-Regno. 425371-11-5 | | | | | | 2.0 | |
| CAS-Regno. 494198-67-3 | | | | | | | |
| CAS-Regno. 803699-05-0 | | | | | | | |
| CAS-Regno. 803699-07-2 | | | | | | | 2.0 |
| CAS-Regno. 803699-09-4 | | | | | | 2.0 | |
| CAS-Regno. 803699-11-8 | | | | | 2.0 | | |
| CAS-Regno. 803699-14-1 | | | | 2.0 | | | |
| CAS-Regno. 803699-15-2 | | | | | 2.0 | | |
| CAS-Regno. 803699-17-4 | | | | | | | 2.0 |
| CAS-Regno. 803699-18-5 | | | | | | | |
| CAS-Regno. 88137-31-9 | | | | | 3.0 | | |
| CAS-Regno. 101220-33-1 | | | | | | 2.0 | |
| CAS-Regno. 875878-17-4 | | | | | | | |
| CAS-Regno. 875878-18-5 | | | | | | | |
| CAS-Regno. 916463-32-6 | | | | | | | 2.0 |
| CAS-Regno. 880761-99-9 | | | | | 2.0 | | |
| CAS-Regno. 880761-95-5 | | | | 2.0 | | | |

Example B4

| INCI-Name | A % w/w | B % w/w | C % w/w | D % w/w | E % w/w | F % w/w | G % w/w |
|---|---|---|---|---|---|---|---|
| C12-15 Alkyl Benzoate | 1.0 | 1.0 | 1.0 | 1.0 | 1.0 | 1.0 | 1.0 |
| Butyl Methoxydibenzoylmethane | 1.0 | 1.0 | 1.0 | 1.0 | 1.0 | 1.0 | 1.0 |
| Octocrylene | 7.5 | 7.5 | 7.5 | 7.5 | 7.5 | 7.5 | 7.5 |
| Neopentyl Glycol Diheptanoate | 6.0 | | 5.0 | | | | |
| Propylene Glycol Dibenzoate | 4.0 | | | | | | |
| Polyester-7 and Neopenthyl Glycol Diheptanoate | | | | | 8.0 | | |
| Diethylhexyl Syringylidenemalonate | | 6.0 | | | | | |
| Polyester 8 | | | 4.0 | | | | |
| Diethylhexyl Malate | | | | 7.0 | | | |
| PPG-3 Myristyl Ether Neoheptanoate | | | | | | 6.0 | |
| Phenethyl Benzoate | | | | | | | 8.0 |
| Isopropyl PPG-2 Isodeceth-7 Carboxylate | | | | | | | |
| Isopropyl C12-15-Pareth-9 Carboxylate | | | | | | | |
| Cetyl PPG-2 Isodeceth-7 Carboxylate | | | | | | | |
| Isohexadecane | 1.5 | 1.5 | 1.5 | 1.5 | 1.5 | 1.5 | 1.5 |
| Cyclopentasiloxane | 2.0 | 2.0 | 2.0 | 2.0 | 2.0 | 2.0 | 2.0 |
| Terephthalylidene Dicamphor Sulfonic Acid | 0.3 | 0.3 | 0.3 | 0.3 | 0.3 | 0.3 | 0.3 |
| Titanium Dioxide particles size 10 to 100 nm | 1.7 | 1.7 | 1.7 | 1.7 | 1.7 | 1.7 | 1.7 |
| Stearic Acid | 0.5 | 0.5 | 0.5 | 0.5 | 0.5 | 0.5 | 0.5 |
| PEG-100 Stearate (and) Glyceryl Stearate | 0.8 | 0.8 | 0.8 | 0.8 | 0.8 | 0.8 | 0.8 |
| Potassium Cetyl Phosphate | 1.3 | 1.3 | 1.3 | 1.3 | 1.3 | 1.3 | 1.3 |
| PVP/Eicosene Copolymer | 1.0 | 1.0 | 1.0 | 1.0 | 1.0 | 1.0 | 1.0 |
| Aqua | Qs to 100 | Qs to 100 | Qs to 100 | Qs to 100 | Qs to 100 | Qs to 100 | Qs to 100 |
| Glycerin | 4.0 | 4.0 | 4.0 | 4.0 | 4.0 | 4.0 | 4.0 |
| Compound of formula (56) or (3) or (12) or (17) or (18) or (19) or (20) or (24) or (30) or (31) or (32) or (35) or (41) or (42) or (43) or (44) or (50) or (51) or (53) | 4.0 | 4.0 | 4.0 | 4.0 | 4.0 | 4.0 | 4.0 |
| 1,1'-(1,4-piperazinediyl)bis[1-[2-[4-(diethylamino)-2-hydroxybenzoyl]phenyl]-methanone (CAS No. 919803-06-8) | 2.0 | 4.0 | 3.0 | 4.0 | 2.0 | 1.0 | 4.0 |
| Micronized 2,4,6-Tris(p-biphenylyl)-s-triazine [CAS No. 31274-51-8] | 5.0 | 9.0 | 3.0 | 1.0 | 7.0 | 2.0 | 15.0 |
| Propylene Glycol | 5.0 | 5.0 | 5.0 | 5.0 | 5.0 | 5.0 | 5.0 |
| Xanthan Gum | 0.2 | 0.2 | 0.2 | 0.2 | 0.2 | 0.2 | 0.2 |
| Acrylates/C10-30 Alkyl Acrylate Crosspolymer | 0.2 | 0.2 | 0.2 | 0.2 | 0.2 | 0.2 | 0.2 |
| Disodium EDTA | 0.2 | 0.2 | 0.2 | 0.2 | 0.2 | 0.2 | 0.2 |
| Triethanolamine | Qs | Qs | Qs | Qs | Qs | Qs | Qs |

-continued

| INCI-Name | A % w/w | B % w/w | C % w/w | D % w/w | E % w/w | F % w/w | G % w/w |
|---|---|---|---|---|---|---|---|
| Dimethicone | 0.4 | 0.4 | 0.4 | 0.4 | 0.4 | 0.4 | 0.4 |
| Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 |
| Tocopheryl Acetate | 0.9 | 0.9 | 0.9 | 0.9 | 0.9 | 0.9 | 0.9 |

Example B5

| INCI-Name | A % w/w | B % w/w | C % w/w | D % w/w | E % w/w | F % w/w | G % w/w |
|---|---|---|---|---|---|---|---|
| Synthetic Beeswax | 0.5 | 0.5 | 0.5 | 0.5 | 0.5 | 0.5 | 0.5 |
| Ethylhexyl Methoxycinnamate | 9.8 | 9.8 | 9.8 | 9.8 | 9.8 | 9.8 | 9.8 |
| Isoamyl p-Methoxycinnamate | 2.0 | 2.0 | 2.0 | 2.0 | 2.0 | 2.0 | 2.0 |
| Ethylhexyl Salicylate | 5.0 | 5.0 | 5.0 | 5.0 | 5.0 | 5.0 | 5.0 |
| Butyl Methoxydibenzoylmethane | 2.8 | 2.8 | 2.8 | 2.8 | 2.8 | 2.8 | 2.8 |
| 4-Methylbenzylidene Camphor | 4.0 | 4.0 | 4.0 | 4.0 | 4.0 | 4.0 | 4.0 |
| Bis-Ethylhexyloxyphenol Methoxyphenyl Triazine | 1.0 | 1.0 | 1.0 | 1.0 | 1.0 | 1.0 | 1.0 |
| Dimethicone | 4.5 | 4.5 | 4.5 | 4.5 | 4.5 | 4.5 | 4.5 |
| Cetearyl Alcohol (and) Dicetyl Phosphate (and) Ceteth-10 Phosphate | 4.5 | 4.5 | 4.5 | 4.5 | 4.5 | 4.5 | 4.5 |
| Cetyl Ricinoleate | 3.0 | 3.0 | 3.0 | 3.0 | 3.0 | 3.0 | 3.0 |
| Butylene Glycol Cocoate | 4.0 | 6.0 | 4.0 | 3.0 | 2.0 | 1.0 | 2.5 |
| Hydroxypropyl Dimethicone Behenate | 2.2 | 2.2 | 2.2 | 2.2 | 2.2 | 2.2 | 2.2 |
| Decyl Cocoate | 1.0 | 1.0 | 1.0 | 1.0 | 1.0 | 1.0 | 1.0 |
| Aqua | Qs to 100 | Qs to 100 | Qs to 100 | Qs to 100 | Qs to 100 | Qs to 100 | Qs to 100 |
| Propylene Glycol | 3.0 | 3.0 | 3.0 | 3.0 | 3.0 | 3.0 | 3.0 |
| Micronized 2,4,6-Tris(p-biphenylyl)-s-triazine [CAS No. 31274-51-8] | 1.0 | 3.0 | 2.0 | 2.0 | 1.0 | 0.5 | 1.0 |
| Micronized 1,1'-(1,4-piperazinediyl)-bis[1-[2-[4-(diethylamino)-2-hydroxy-benzoyl]phenyl]-methanone (CAS No. 919803-06-8) | 3.0 | 1.0 | 1.0 | 4.0 | 2.0 | 1.0 | 3.0 |
| Compound of formula (56) or (3) or (12) or (17) or (18) or (19) or (20) or (24) or (30) or (31) or (32) or (35) or (41) or (42) or (43) or (44) or (50) or (51) or (53) | 4.0 | 3.0 | 2.0 | 1.0 | 3.0 | 5.0 | 3.0 |
| Octocrylene | 2.0 | 4.0 | 6.0 | 8.0 | 10.0 | 10.0 | 8.0 |
| Decyl Glucoside | 0.5 | 0.5 | 0.5 | 0.5 | 0.5 | 0.5 | 0.5 |
| Ammonium Acryloyldimethyltaurate/-VP Copolymer | 0.3 | 0.3 | 0.3 | 0.3 | 0.3 | 0.3 | 0.3 |
| Phenylbenzimidazole Sulfonic Acid | 2.0 | 2.0 | 2.0 | 2.0 | 2.0 | 2.0 | 2.0 |
| Acrylates/C10-30 Alkyl Acrylate Crosspolymer | 0.2 | 0.2 | 0.2 | 0.2 | 0.2 | 0.2 | 0.2 |
| Disodium EDTA | 0.2 | 0.2 | 0.2 | 0.2 | 0.2 | 0.2 | 0.2 |
| Methylene Bis-Benzotriazolyl Tetramethylbutylphenol | 5.0 | 5.0 | 5.0 | 5.0 | 5.0 | 5.0 | 5.0 |
| Trometamine | 0.8 | 0.8 | 0.8 | 0.8 | 0.8 | 0.8 | 0.8 |
| Styrene/Acrylates Copolymer | 5.0 | | | | | 3.0 | |
| PEG-6 Isostearate (and) Hesperetin Laurate | | 3.0 | | | | 1.0 | 4.0 |
| Polyacrylate-15 (and) Polyacrylate-17 | | | 4.0 | | | | |
| Carthamus Tinctorius (Safflower) Oleosomes | | | | 5.0 | | | |
| PTFE | | | | | 4.0 | | |
| Cyclohexasiloxane (and) Cyclopentasiloxane | 0.8 | 0.8 | 0.8 | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 | 0.8 | 0.8 | 0.8 |
| Tocopheryl Acetate | 0.4 | 0.4 | 0.4 | 0.4 | 0.4 | 0.4 | 0.4 |

The invention claimed is:

1. A Cosmetic composition comprising
a) at least one compound of formula (1)

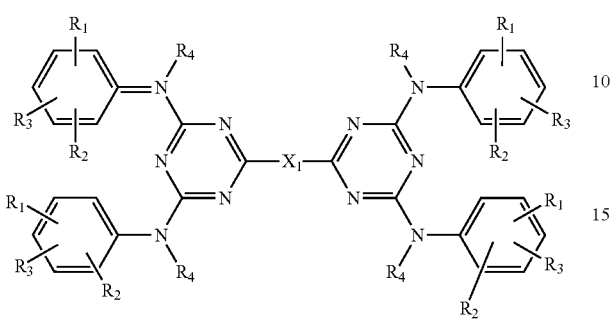

wherein
$X_1$ is a bivalent radical of formula

   (1a)

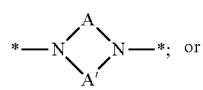   (1b)

   (1c)

A in (1a) and (1c) is independently unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene; or $C_5$-$C_{10}$arylene-($C_1$-$C_{12}$alkylene);

A and A' in (1b) independently from each other are unsubstituted or substituted, straight-chain or branched $C_1$-$C_{12}$alkylene;

$R_1$ is a radical of formula

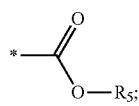   (1d)

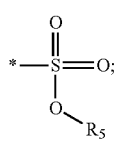   (1e)

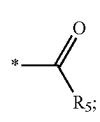   (1f)

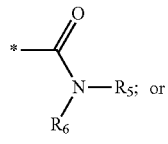   (1g)

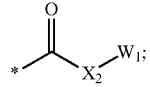   (1h)

$R_2$ and $R_3$ independently from each other are hydrogen; $C_1$-$C_{12}$alkyl; $OR_7$; $NR_7R_8$; or $C_6$-$C_{10}$aryl;
$X_2$ is O, or NH;
$W_1$ is $C_1$-$C_{20}$alkyl; or a group Sp-Sil;
Sp is a straight-chain or branched saturated or single or multiple unsaturated $C_3$-$C_{12}$ hydrocarbon;
Sil is a silane; an oligosiloxane; or a polysiloxane moiety; and
$R_4$, $R_5$, $R_6$, $R_7$, $R_8$ and $R_9$ independently from each other are hydrogen; $C_1$-$C_{12}$alkyl; or $C_3$-$C_{12}$cycloalkyl; and
b) cosmetically tolerable carriers or adjuvants.

2. The composition according to claim 1 wherein $R_1$ is a radical of formula

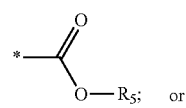   (1d)

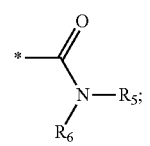   (1g)

wherein
$R_5$ and $R_6$ independently from each other are hydrogen; or $C_1$-$C_5$alkyl.

3. The composition according to claim 2, wherein
$R_5$ is $C_1$-$C_5$alkyl; or hydrogen; and
$R_6$ is hydrogen.

4. The composition according to claim 1, wherein
$X_1$ is a radical of formula (1b), wherein
A and A' are $C_1$-$C_4$alkylene.

5. The composition according to claim 1, wherein
$X_1$ is a radical of formula (1a), wherein
A is $C_1$-$C_5$alkylene; or phenylene; and
$R_9$ is hydrogen.

6. The composition according to claim 1, wherein $X_1$ is selected from

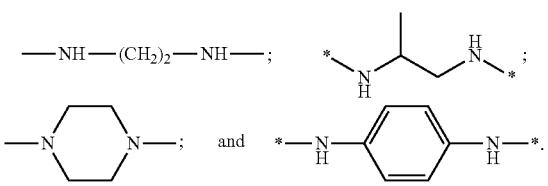

7. The composition according to claim 1, wherein
$R_2$, $R_3$ and $R_4$ are hydrogen.

8. The composition according to claim 1, wherein
Sil is the group $SiR_{10}R_{11}R_{12}$, wherein
$R_{10}$, $R_{11}$ and $R_{12}$ each independently are $C_1$-$C_6$alkyl; $C_1$-$C_6$alkoxy; or phenyl; or an oligosiloxane of formula $-SiMe_m(OSiMe_3)_n$; or an oligosiloxane of the formulae

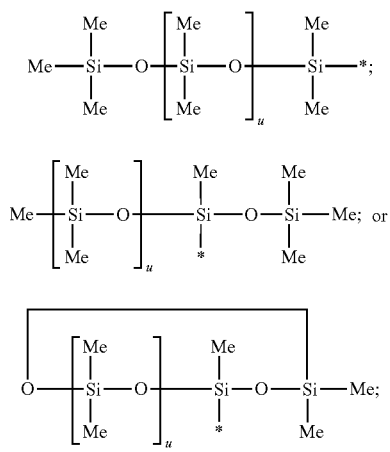

(1i)

(1k)

(1l)

wherein

Me is methyl;

m is 0; 1; or 2;

n is 1; 2; or 3;

m+n are 3; and u is 0 to 6.

9. The composition according to claim 1, which conform to formula (2)

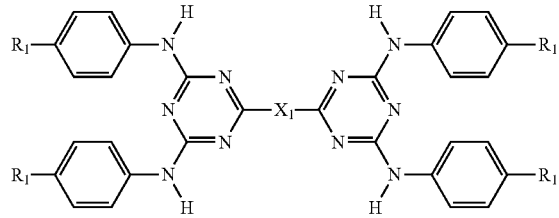

wherein $R_1$ is a radical of formula

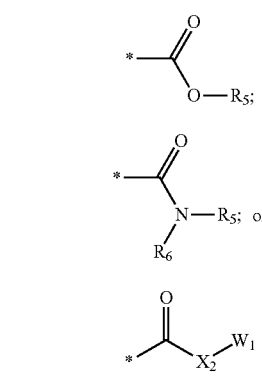

$X_1$ is radical of formula (1a) —$NR_9$-A-$NR_9$—; (1c) *—O-A-O—*; or

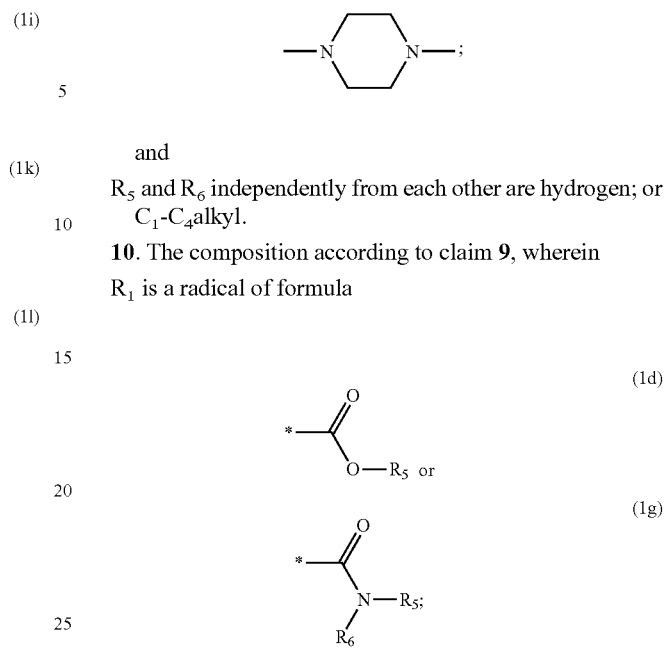

and $R_5$ and $R_6$ independently from each other are hydrogen; or $C_1$-$C_4$alkyl.

10. The composition according to claim 9, wherein $R_1$ is a radical of formula

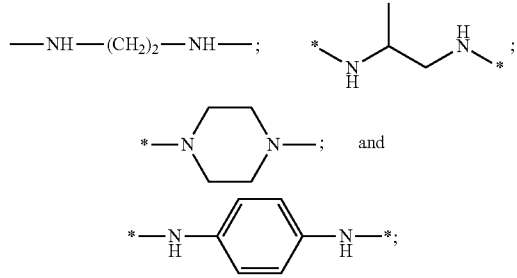

$X_1$ is selected from

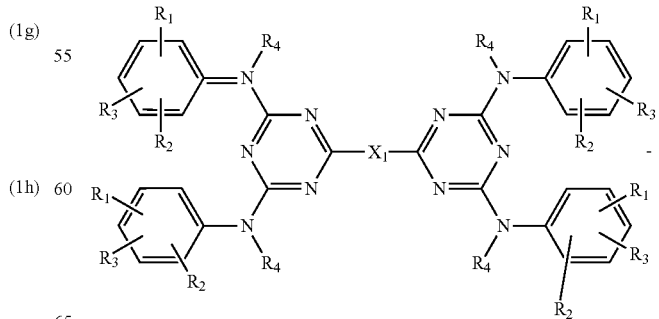

and $R_5$ and $R_6$ independently from each other are hydrogen; or $C_1$-$C_4$alkyl.

11. A process for the preparation of a compound of formula (1), (1)

wherein $X_1$ is a bivalent radical of formula

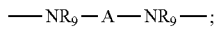 (1a)

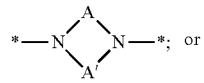 (1b)

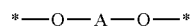 (1c)

A in (1a) and (1c) is independently unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene-($C_1$-$C_{12}$alkylene);

A and A' in (1b) independently from each other are unsubstituted or substituted, straight-chain or branched $C_1$-$C_{12}$alkylene;

$R_1$ is a radical of formula

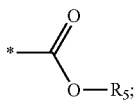 (1d)

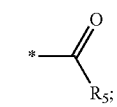 (1f)

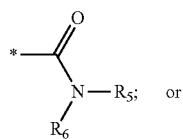 (1g)

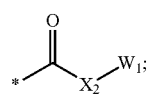 (1h)

$R_2$ and $R_3$ independently from each other are hydrogen; $C_1$-$C_{12}$alkyl; $OR_7$; $NR_7R_8$; or $C_6$-$C_{10}$aryl;

$X_2$ is O, or NH;

$W_1$ is $C_1$-$C_{20}$alkyl; or a group Sp-Sil;

Sp is a straight-chain or branched saturated or single or multiple unsaturated $C_3$-$C_{12}$ hydrocarbon;

Sil is a silane; an oliqosiloxane; or a polysiloxane moiety; and $R_4$, $R_5$, $R_6$, $R_7$, $R_8$ and $R_9$ independently from each other are hydrogen; $C_1$-$C_{12}$alkyl; or $C_3$-$C_{12}$cycloalkyl;

which process comprises reacting 2 moles of a chlorotriazine of formula (1m) with 1 mole of a compound of formula (1n) according to the following reaction scheme:

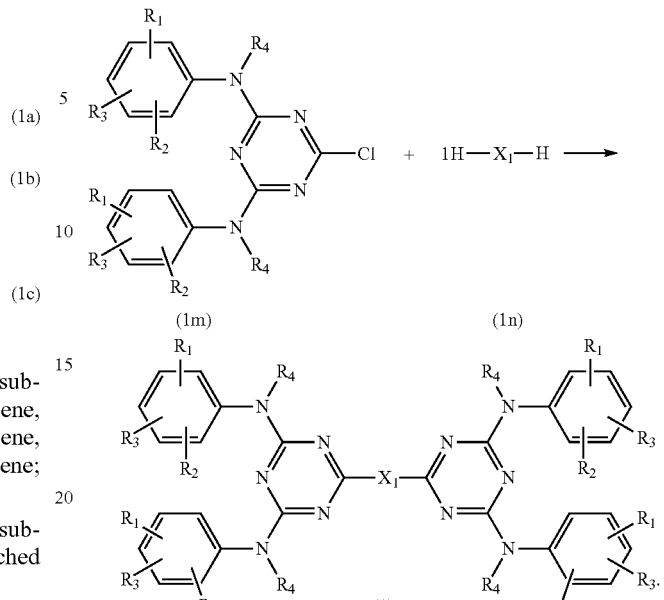

12. A process for the preparation of a micronized compound of formula (1)

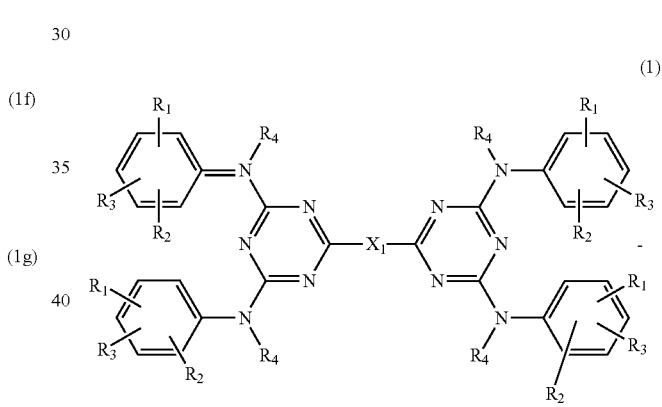

wherein $X_1$ is a bivalent radical of formula

 (1a)

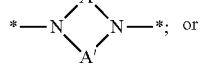 (1b)

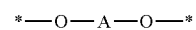 (1c)

A in (1a) and (1c) is independently unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene; or $C_5$-$C_{10}$arylene-($C_1$-$C_{12}$alkylene);

A and A' in (1b) independently from each other are unsubstituted or substituted, straight-chain or branched $C_1$-$C_{12}$alkylene;

$R_1$ is a radical of formula

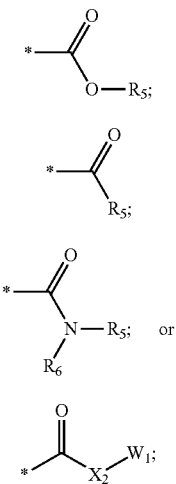

$R_2$ and $R_3$ independently from each other are hydrogen; $C_1$-$C_{12}$alkyl; $OR_7$; $NR_7R_8$; or $C_6$-$C_{10}$aryl;
$X_2$ is O, or NH;
$W_1$ is $C_1$-$C_{20}$alkyl; or a group Sp-Sil;
Sp is a straight-chain or branched saturated or single or multiple unsaturated $C_3$-$C_{12}$ hydrocarbon;
Sil is a silane; an oligosiloxane; or a polysiloxane moiety; and
$R_4$, $R_5$, $R_6$, $R_7$, $R_8$ and $R_9$ independently from each other and hydrogen; $C_1$-$C_{12}$alkyl; or $C_3$-$C_{12}$cycloalkyl;
comprising wet-milling, wet-kneading, spray-drying from a suitable solvent, by expansion according to the RESS process or by reprecipitation from suitable solvents of the compound of formula (1) to obtain microparticles having a mean particle size from 0.02 to 2 µm.

13. The cosmetic composition according to claim 1 wherein at least one compound of formula (1) is present in the composition in a micronized state.

14. A UV absorber dispersion, comprising
(a) at least one micronised UV absorber of formula (1)

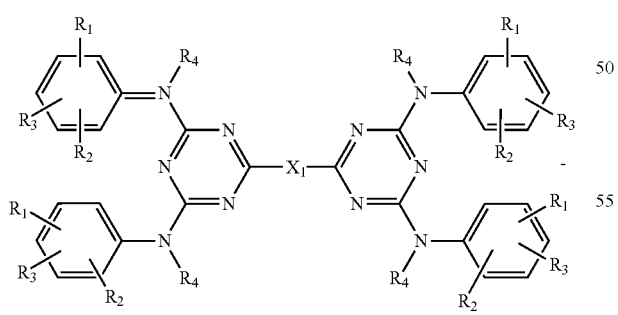

wherein
$X_1$ is a bivalent radical of formula

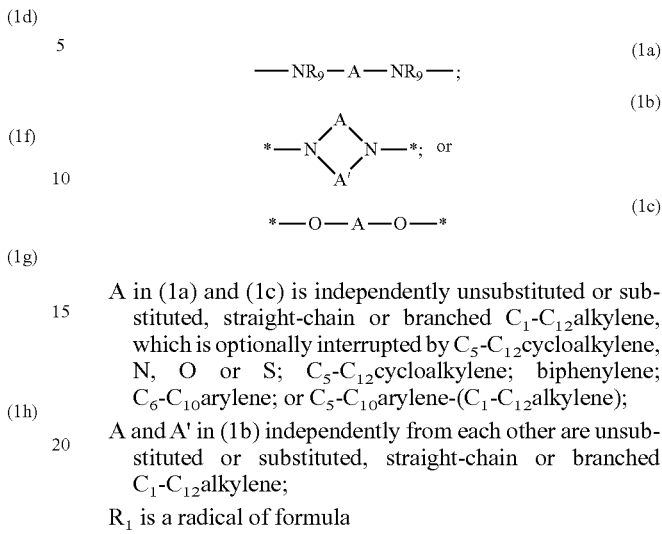

A in (1a) and (1c) is independently unsubstituted or substituted, straight-chain or branched $C_1$-$C_{12}$alkylene, which is optionally interrupted by $C_5$-$C_{12}$cycloalkylene, N, O or S; $C_5$-$C_{12}$cycloalkylene; biphenylene; $C_6$-$C_{10}$arylene; or $C_5$-$C_{10}$arylene-($C_1$-$C_{12}$alkylene);
A and A' in (1b) independently from each other are unsubstituted or substituted, straight-chain or branched $C_1$-$C_{12}$alkylene;
$R_1$ is a radical of formula

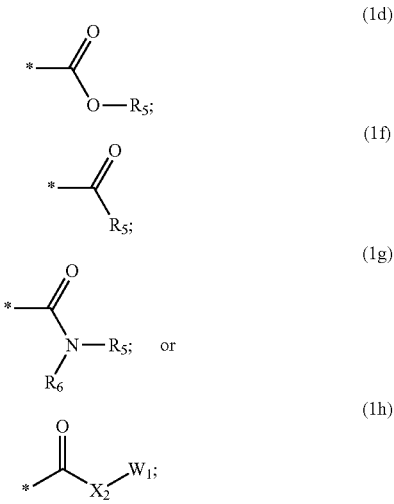

$R_2$ and $R_3$ independently from each other are hydrogen; $C_1$-$C_{12}$alkyl; $OR_7$; $NR_7R_8$; or $C_6$-$C_{10}$aryl;
$X_2$ is O, or NH;
$W_1$ is $C_1$-$C_{20}$alkyl; or a group Sp-Sil;
Sp is a straight-chain or branched saturated or single or multiple unsaturated $C_3$-$C_{12}$ hydrocarbon;
Sil is a silane; an oligosiloxane; or a polysiloxane moiety; and
$R_4$, $R_5$, $R_6$, $R_7$, $R_8$ and $R_9$ independently from each other are hydrogen; $C_1$-$C_{12}$alkyl; or $C_3$-$C_{12}$cycloalkyl;
having a particle size from 0.02 to 2 µm, and
(b) a suitable dispersing agent.

* * * * *